(12) United States Patent
Mallick et al.

(10) Patent No.: US 9,058,765 B1
(45) Date of Patent: Jun. 16, 2015

(54) SYSTEM AND METHOD FOR CREATING AND SHARING PERSONALIZED VIRTUAL MAKEOVERS

(75) Inventors: Satya Mallick, San Diego, CA (US); Kevin Barnes, San Diego, CA (US); David Kriegman, San Diego, CA (US)

(73) Assignee: TAAZ, INC., La Jolla, CA (US)

( * ) Notice: Subject to any disclaimer, the term of this patent is extended or adjusted under 35 U.S.C. 154(b) by 1058 days.

(21) Appl. No.: 12/406,099

(22) Filed: Mar. 17, 2009

Related U.S. Application Data

(60) Provisional application No. 61/037,323, filed on Mar. 17, 2008, provisional application No. 61/037,319, filed on Mar. 17, 2008, provisional application No. 61/037,314, filed on Mar. 17, 2008.

(51) Int. Cl.
*G09G 5/00* (2006.01)
*G09G 5/14* (2006.01)

(52) U.S. Cl.
CPC .............. *G09G 5/14* (2013.01); *G09G 2340/10* (2013.01)

(58) Field of Classification Search
None
See application file for complete search history.

(56) References Cited

U.S. PATENT DOCUMENTS

| | | | |
|---|---|---|---|
| 5,280,530 A * | 1/1994 | Trew et al. ................... 382/103 |
| 5,893,373 A | 4/1999 | Reynolds |
| 5,924,426 A | 7/1999 | Galazin |
| 6,000,407 A | 12/1999 | Galazin |
| 6,293,284 B1 | 9/2001 | Rigg |
| 6,697,518 B2 | 2/2004 | Belhumeur et al. |
| 7,079,158 B2 * | 7/2006 | Lambertsen ................... 345/630 |
| 7,121,429 B2 * | 10/2006 | Bartholomew et al. ........... 222/1 |
| 7,324,668 B2 * | 1/2008 | Rubinstenn et al. .......... 382/118 |
| 7,412,105 B2 * | 8/2008 | Wilensky ....................... 382/254 |
| 7,418,371 B2 * | 8/2008 | Choe et al. ........................ 703/2 |
| 7,437,344 B2 * | 10/2008 | Peyrelevade .................... 706/62 |
| 7,958,066 B2 * | 6/2011 | Pinckney et al. ............... 706/12 |
| 8,077,931 B1 * | 12/2011 | Chatman et al. ............... 382/118 |
| 2001/0037191 A1 * | 11/2001 | Furuta et al. ..................... 703/6 |
| 2003/0063794 A1 * | 4/2003 | Rubinstenn et al. .......... 382/154 |
| 2003/0095701 A1 * | 5/2003 | Shum et al. ................... 382/155 |
| 2003/0223622 A1 * | 12/2003 | Simon et al. .................. 382/118 |
| 2005/0203724 A1 * | 9/2005 | Orpaz et al. ...................... 703/6 |

(Continued)

OTHER PUBLICATIONS

Celebrity Beauty Secret Goldmin, Virtual Makeovers & Makeover Games, 2007, www.celebrity-beauty-tip-goldmine.com, as of Jan. 31, 2008.

(Continued)

*Primary Examiner* — Aaron M Richer
*Assistant Examiner* — Anh-Tuan V Nguyen
(74) *Attorney, Agent, or Firm* — Cotman IP Law Group, PLC

(57) ABSTRACT

A system and methods for creating and sharing personalized virtual makeovers comprising algorithms for applying virtual cosmetics, hairstyles and accessories to a digital portrait of an individual using described techniques that produce a revised image with a realistic appearance. The system may calculate positions of the boundaries of facial features such as eyes, lips and hair, or provide the user a sophisticated adjustment method. The invention places and shapes virtual cosmetics, hairstyles and accessories to precisely calculated locations, blending colors and shading for a realistic and lifelike result. Accessories such as eyeglasses and jewelry are also realistically applied. The system comprises individual makeover editors for skin, eyes, lips, hair and accessories. Virtual makeovers may be shared, including allowing multiple users modify the same image simultaneously.

47 Claims, 9 Drawing Sheets

(56) References Cited

U.S. PATENT DOCUMENTS

| | | | |
|---|---|---|---|
| 2006/0197775 A1* | 9/2006 | Neal | 345/589 |
| 2006/0268101 A1* | 11/2006 | He et al. | 348/14.12 |
| 2007/0019882 A1* | 1/2007 | Tanaka et al. | 382/276 |
| 2007/0083819 A1* | 4/2007 | Shoemaker | 715/767 |
| 2007/0189627 A1* | 8/2007 | Cohen et al. | 382/254 |
| 2007/0258656 A1* | 11/2007 | Aarabi | 382/254 |
| 2008/0024505 A1* | 1/2008 | Gordon et al. | 345/473 |
| 2008/0218532 A1* | 9/2008 | Young | 345/660 |
| 2008/0297519 A1* | 12/2008 | Scapel et al. | 345/474 |
| 2009/0087035 A1* | 4/2009 | Wen et al. | 382/118 |

OTHER PUBLICATIONS

Greenberg, et al., A Framework for Realistic Image Synthesis, SIGGRAPH 97 Conference Proceedings, Annual Series, pp. 477-494, Aug. 1997.

Gardner, Brian, Six Things, Rapid Fire #1: Photo-Realistic, Mar. 6, 2006, www.brownbatterystudios.com, as of Mar. 11, 2008.

* cited by examiner

SYSTEM AND METHOD FOR CREATING AND SHARING PERSONALIZED VIRTUAL MAKEOVERS

CROSS REFERENCE TO RELATED APPLICATIONS

This application claims priority to three U.S. Provisional Patent Applications, all filed on Mar. 17, 2008, and all co-owned by the same assignee. These applications are entitled "SYSTEM AND METHOD FOR CREATING AND SHARING PERSONALIZED VIRTUAL MAKEOVERS," Ser. No. 61/037,323, "GRAPHICAL USER INTERFACE FOR SELECTION OF OPTIONS FROM OPTION GROUPS AND METHODS RELATING TO SAME," Ser. No. 61/037,319, and "METHOD OF MONETIZING ONLINE PERSONALIZED BEAUTY PRODUCT SELECTIONS," Ser. No. 61/037,314, filed 17 Mar. 2008. These provisional patent applications are hereby incorporated by reference in their entirety into this specification.

BACKGROUND OF THE INVENTION

1. Field of the Invention

Embodiments of the invention described here pertain to the field of computer systems. More particularly, but not by way of limitation, one or more embodiments of the invention enable a system and methods for creating and sharing personalized virtual makeovers through the application of virtual cosmetics, hairstyles and accessories to a digital portrait.

2. Description of the Related Art

Virtual makeover websites are popular web destinations. Most well-known existing programs allow users to perform basic, though sometimes crude editing of a digital portrait using a graphical user interface to apply colors ("makeup"), cutouts of hair ("hairstyles"), or eyeglasses to the portrait to easily change the appearance, style or "look" of the person in the portrait. However, the technology available to alter portraits in such programs rarely produces a lifelike result (or "look.") As used here, the term "look," means the appearance of a person as determined by fashionable or stylistic standards achieved by applications of, including but not limited to: makeup, hairstyle and hair color. Thus, the term "look" is used here as a noun, in the colloquial sense, to describe a person's overall style or appearance. As such, giving the subject of the image a "makeover" would be to graphically edit a digital image to give the subject a "new look." The term "makeover," as used here, means an overall beauty treatment involving a person's hairstyle, cosmetics, face paints, tattoos, clothing and jewelry and accessories including glasses, hats, head gear, contact lenses, piercings, for example, intended to change or improve a person's appearance. Creating a "new look" may include changes beyond makeup and hairstyles, such as adding or removing accessories such as color contact lens, eyeglasses, or hats. In some instances changing accessories alone may create a new "look."

While many sophisticated computer programs exist for digital photograph editing, there is a need for an easy-to-use virtual makeover system and methods that produce a lifelike personalized rendering of an individual using simple, intuitive library of tools and images to provide desirable cosmetics, hairstyles and/or accessories for application to portraits without requiring the user to learn a complex graphic editor application. As used here, the term "lifelike" means "resembling or simulating real life; appearing as in a digital image that has not been retouched or graphically modified; a digital rendition of human face that appears to be of photographic quality; a high fidelity image; realistic in appearance." The term "photorealistic rendering" or "photorealistic" is used in the general sense of its meaning in computer graphics, typically defined to mean, "[r]endering images so that they closely resemble a photograph; such renderings take into account reflective properties, light sources, illumination, shadows, transparency and mutual illumination." However, the term photorealistic, as used here, is also used in the sense that is well understood by those of ordinary skill in the art of computer graphics and as such may include but is not limited to that definition.

Existing virtual makeover programs may allow for the application of hairstyles, colors, lipstick, lip liner, teeth whitening, eye shadow, eyeliner, blush, contacts, glasses and headwear to be applied to a digital image. A comprehensive list of such changes, referred to in part as "makeover item(s)," is described below. However, these items may not be properly scaled or warped to conform to the subject of the image.

The makeover items in some existing virtual makeover programs may be applied to photographs that are not brightness/color corrected. Further, generally haphazardly positioned and sized makeover items such as hairstyles are often not blended into the images so that the resulting views are not lifelike or pleasing. Perhaps this is because most known makeover programs and websites do not appear to calculate the precise locations of facial features, their application of cosmetics, styles and accessories to an image is prone to translational and shape errors that are readily apparent to the human eye. In addition, with respect to positioning of cosmetics, hairstyles and accessories on a face in a digital image, these items often overlap existing portions of the face that should not be covered. For example, applying eye shadow in one or more existing makeover websites results in the application of color to the eyebrows since the exact positions of the eyebrows are not calculated.

Most known makeover websites provide the ability to apply cutout overlays of hair to digital images that may not be sized, oriented, automatically aligned, or otherwise adjusted to result in a believable image. Such "cartoon" shape and placement of hairstyles and other makeover items create a false impression and may not create a desire to purchase products. In addition, current programs may not automatically blend or correct for the color, brightness, and other lighting aspects of the original image, nor align the placement of cosmetics, styles and accessories to the face in a digital image. The resulting images from such systems are perceptually altered, appearing unnatural or cartoonish to the human eye and thus are not useful for selecting a makeover look.

Application of accessories, for example, may suffer from the same disadvantages in the prior art as other makeover items. Some programs that attempt to place accessories on a portrait do not produce lifelike shadows, correct lighting color or face angle to the camera, and hence the resulting look may not produce a believable or pleasing image. Application of sunglasses to a face turned slightly in profile in such existing systems, for example, may produce a cardboard-cutout looking rendering where the sunglasses image may not be brightness-corrected to work with the underlying digital image, and as such that the resulting image may not appear lifelike. Similarly, application of other accessories, such as a hat for example, where the hat was photographed under one set of lighting conditions while the portrait was captured under a different set of light conditions may produce a resulting image that appears to have cutout overlays that are not lifelike.

For at least the limitations described above, there is a need for an easy-to-use but sophisticated system and methods for creating and sharing personalized virtual makeovers through the application of virtual cosmetics, hairstyles and accessories to portraits of an individual for entertainment and for commercial purposes.

SUMMARY OF THE INVENTION

One or more embodiments of the invention enable a system and methods for creating and sharing personalized virtual makeovers. The personalized virtual makeovers are created through the application of virtual cosmetics, hairstyles and accessories to one or more graphic layers that are displayed "over" the portrait. Saved images may or may not be combined with the overlay layers to render a single digital image. The system may calculate positions for areas of a face in a portrait, for example, and may also determine the location of pixels for the boundaries of skin, eyes, lips and hair. The system calculates positions to enable accurate application and adjustment of virtual cosmetics, hairstyles and accessories at preferred locations within the portrait. For example, in one or more embodiments of the invention, hair color and skin tones may be graphically blended at the top of the forehead to eliminate a "cutout" appearance at the boundaries.

In addition, the portrait may be analyzed in one or more embodiments of the invention to calculate the light source color and/or direction in the portrait. One or more embodiments of the invention may normalize the portrait with respect to the light source color, angle and brightness. A normalized portrait allows for the application of cosmetics, styles and accessories that are independent of the shading, brightness or light color or angle associated with the original portrait.

One or more embodiments may blend cosmetics, hairstyles and accessories as captured from different light directions onto a portrait to maintain the original light color and light direction. As used here accessories may include, but are not limited to: glasses, hats, scarves, hair clips, hair appliances, jewelry, moles, face paints, piercings, tattoos, false eyelashes, veneers and color contact lenses. Because portraits in the invention do not require a face to be looking directly at the device that captured the portrait, the invention may comprise a library of images of hairstyles and accessories that have been taken at various angles to allow for their application to portraits captured at less than a "full face forward" (also called frontal) orientation. The resulting look from a preferred embodiment may be photorealistic and lifelike, rendering an attractive virtual makeover.

Creation and modification of makeovers may be performed by the system using makeover editors. Available makeover items may be divided into a number of specialized groups to facilitate use in editing particular parts of a portrait. These groups may be collected into particularized editors that provide a convenient user interface for interacting with particular kinds of makeover items. In one or more embodiments, the makeover program may provide skin, eye, mouth, hair and accessory editors. Skin makeover editing may include makeover items such as foundation, concealer, and blush. Eye makeover editing may be performed through the application of makeover items such as eye shadow, eyeliner, mascara, and colored contact lens. Mouth makeover editing may be performed through the application of makeover items such as lipstick, lip liner, lip-gloss, lip plumping and teeth whitening and straightening. Sophisticated hairstyle makeover editing may be performed by the makeover program through the application of makeover items such as a hairstyle, hair color, and hair accessories. In one or more embodiments, the makeover program may provide controls to allow the user to shape the hairstyle to the head in the portrait. Accessory makeover editing may be performed through the application of accessory makeover items to the portrait. Accessories may include items such as eyeglasses, jewelry, clothing such as hats, headbands, or hair clips, as well as tattoos and piercings. Accessory editing may comprise size adjustments, rotation, color changes, or placement location of various accessories available to the makeover program through a library of accessory photographs. Makeover editors present options for the placement of makeover items particularly calculated to the item type. For example, various elements such as for example blush, may be positioned based on calculated locations on the portrait, and then rendered on the image by one or more embodiments of the invention in a photorealistic manner in a style selected by the user.

One or more embodiments of the invention may be configured to provide attractive recommendations for colors and styles based on the colors and shapes associated with a face in a portrait. For example, for faces of a certain shape such as a round face, makeovers associated with others having the same basic face shape may be presented to the user to allow for simple selection of a compatible look. Makeovers may be assigned popularity values and the most popular makeovers may be presented by the system as examples. Popular makeovers may be filtered to present only those makeovers that are applicable to the user based on a portrait of the user. In addition, celebrity looks may be presented to allow for the selection of the look of a famous celebrity.

One or more embodiments of the methods of the invention work by obtaining a portrait, detecting various facial characteristics within the portrait, providing a makeover item to apply to the face in the portrait and combining the makeover item to the face in a photorealistic manner. As used here, facial characteristics may include, but are not limited to: skin color, eye color, eyebrow color, hair color, facial hair color, face shape, distance between outer corners of eye, eye shape, nose shape, nose width, nose length, lip thickness, mouth width, teeth color, ear position, ear shape, ear size. One or more embodiments of the invention are capable of detecting facial boundaries of a face in the portrait, detecting eye and mouth boundaries within the facial boundaries and detecting skin tone and light color and light direction associated with the face in the portrait, either automatically or semi-automatically.

BRIEF DESCRIPTION OF THE DRAWINGS

The above and other aspects, features and advantages of the invention will be more apparent from the following more particular description thereof, presented in conjunction with the following drawings where.

DETAILED DESCRIPTION

Figure 1:
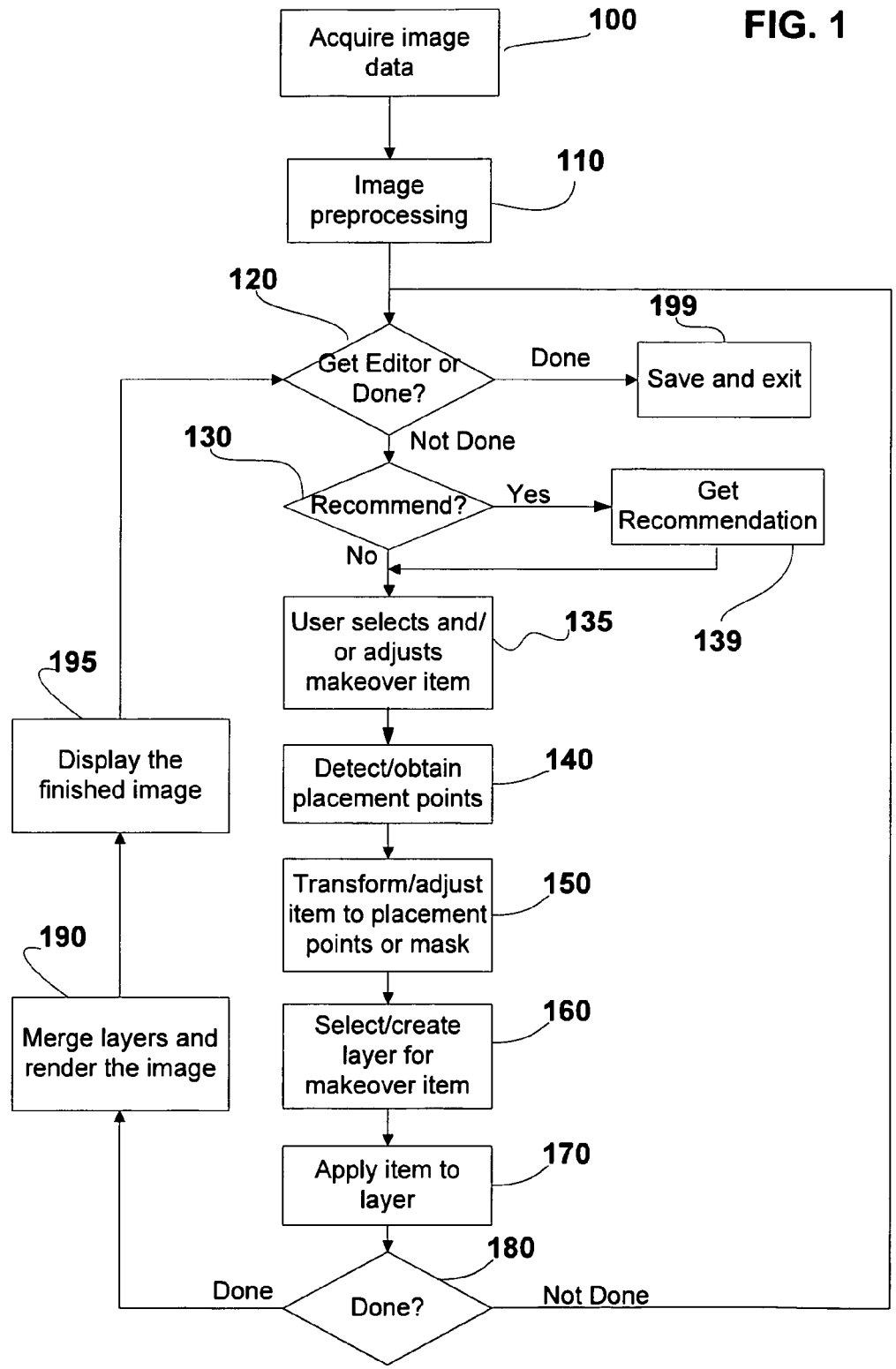
FIG. 1 illustrates an overview of one or more methods of various embodiment of the invention.

A system and methods for creating and sharing personalized virtual makeovers through the application of virtual cosmetics, hairstyles and accessories to portraits will now be described. In the following exemplary description, numerous specific details are set forth in order to provide a more thorough understanding of embodiments of the invention. It will be apparent, however, to an artisan of ordinary skill that the invention may be practiced without incorporating all aspects of the specific details described here. In other instances, specific features, quantities, or measurements well known to those of ordinary skill in the art have not been described in detail so as not to obscure the invention. Readers should note that although examples of the invention are set forth here, the claims, and the full scope of any equivalents, are what define the metes and bounds of the invention.

Virtual Makeovers Overview

Embodiments of the system and methods described enable personalized virtual makeovers to be created through the application of virtual cosmetics, hairstyles and accessories to one or more portraits. The term "portrait," as used here, means an image of a subject being submitted for a makeover. The terms "portrait" and "image" may be used interchangeably in this description. A portrait in the spirit of the invention may include a digital or scanned photograph, a cartoon, line drawing, avatar or other representation of a subject for makeover. The subject need not be human, but may be an animal, or fantasy avatar, or other image to which the user wishes to perform sophisticated appearance editing. As used herein, the term "program" or "makeover program" refers to one or more computers, servers, or other type of digital processing device or devices, such as kiosks, cell phones, game consoles, handheld computers or personal data assistants, for example, specially programmed to implement the system and methods of one or more embodiments of the invention, and may be used for clarity and not as a limitation thereof.

As used here, the term "makeover" refers to changing one's appearance, sometimes through changes to cosmetics, accessories, hairstyles and/or alterations. Makeovers may range from something as simple as a new haircut or makeup, to the use of eye-color-changing contact lenses. More extreme changes such as would be made by the implantation of dental veneers, cosmetic or plastic surgery, or the appearance-altering effect of significant weight loss is also within the scope and spirit of the invention. However, the examples presented here perform makeovers in the sense of popular television shows. However, such examples in no way limit the extent of the invention, which is defined by the claims attached hereto.

The term "Virtual Makeover" is used herein in its colloquial sense to refer to makeovers performed by computer software. Typically, virtual makeover programs import a photograph of a human face. The user may then use the software to apply cosmetics, hairstyles, and accessories such as eyewear to affect a makeover, allowing the user to visualize different looks without physically trying them on.

The more advanced virtual makeover program of the invention (hereinafter, "the virtual makeover program" or "the invention") may be performed by a specially programmed computer or computer system performing the methods described here to allow users to virtually "try on" colors, styles, and accessories in an accurate and lifelike ("photorealistic") rendition to see how the new look or style may appear without shopping or other effort. The system and methods of the makeover program described herein are useful in creating a desire to purchase new cosmetics, hair styles and accessories in consumers without the time, patience or ability to directly interact with a multitude of products and services that may be available online. These users may get a first impression that creates consumer desire for products and services. Furthermore, while the examples of virtual makeovers presented here are described in terms of a web-based program, the makeover program is not so limited, as will be well understood by those of ordinary skill in the art. Makeovers of the makeover program described herein may share or gift makeovers to others and in one or more embodiments may also be used to render 3D models of a subject for better fit or modeling of an accessory, look or style, and may also be useful for other commercial and scientific purposes.

Overview of the Various Methods

One or more embodiments of the makeover program are directed towards the implementation of methods and algorithms that enable users to apply a virtual makeover to an image. When doing so users are able to try out different looks using varying colors and types of makeup and thereby get an initial first impression of how a particular color, brand or style of application might look. As used herein, the term "user" is used in its loosest sense to mean a director of the activities of the system and method of the invention. In one or more embodiments, a "user" may be a person, a group of people, or a computer program or other intelligence directing the choices describe here. For simplicity of description the selections to be made will be described as a "user," but the makeover program is not limited to a single person directing the available choice selections.

Conceptually, one or more methods of the makeover program for creating a virtual makeover involves obtaining a digital image ("portrait") for processing, determining what areas of the portrait most closely resemble skin tones, identifying the area of the image that contain facial features, in some embodiments detecting skin tones and facial features or in others via user input. The user may then select one or more editors to use to alter the image. The editors operate on one or more graphics layers, conceptually above the image, applying changes such as hairstyle, makeup and accessories in various layers at the user's direction and control. Layers may be applied to the image when the user saves the makeover. Novel aspects of selection, identification, detection and alteration of the facial features, as well as methods for the transformation and management of makeover items such as hairstyles, makeup, and accessories, for example, are described herein. As used herein, the term "makeover items(s)" may include but is not limited to such desirable alterations as: hairstyles, hair color, hair highlight and low lights, hair accessories, lipstick, lip liner, lip gloss, lip plumper, teeth whitening, dental veneers or other teeth corrections, eye shadow, eyeliner, eye brow pencil, mascara, under eye concealer, colored contact lens, eye glasses, sunglasses, blush, foundation, spot concealer, and bronzer, for example. Makeover items in the spirit of the invention may also include clothing, outer ware such as hats and scarves, and fashion accessories such as: headwear, jewelry, tattoos, face paints, and piercings, for example. The specific details for implementing each of the conceptual steps of the methods of the invention will now be set forth in the following description.

FIG. 1 illustrates a conceptual overview process of a computer or computer system particularly programmed to perform one or more methods of the invention. While the process is described as a step-by-step method here, the steps where logical may be performed in alternate orders befitting an event driven architecture. A graphic user interface for supporting the methods, algorithms of the invention may be found in U.S. Provisional Application 61/037,319—elsewhere herein incorporated by reference.

At step 100, as shown in FIG. 1, the makeover program acquires image data, either from the user inputting image data into the system by any of numerous methods well known to those in the art of computer use, or from a file, a bit stream, directly from a connected or remote device, or any other method known to those of skill in the art. At step 110, the image may be preprocessed to locate placement point(s) in the image. This step may be performed by a user, or may be performed automatically by the makeover program. Part of the preprocessing step includes correction of the image for color balance, light source and normalization of the image for the light source. Other aspects of the preprocessing include accurate detection or identification of facial features in the portrait.

At step 120, the user selects a desired makeover-editing module to edit the image. At step 130, one or more embodiments may offer to provide recommendations, as detailed elsewhere herein. If the user selects a recommendation, the recommendation engine provides recommended makeover items to the user at step 139. Makeover-editing modules may include, for example, hair, lips, skin, eyes, blush, foundation, concealer, and accessory editors. From the makeover-editing module, the user selects or adjusts the makeover item at step 135. This choice may be made by a user, or may be recommended by a makeover recommendation engine from step 139. A makeover recommendation engine may be part of the makeover program, or a separate program, which may be part of the computer system or program designed to perform the methods described here, and may be described in detail later in this specification.

At step 140 the makeover program detects or obtains the placement points for the makeover item selected. In one or more embodiments, establishment of placement points was performed as part of Preprocessing Step 110. In other embodiments, the makeover program may automatically detect the placement points. At step 150, the makeover program transforms the selected makeover item so that its position conforms to the locations of the placement points. The makeover program may perform this step automatically, or the user may transform the item interactively in one or more embodiments.

At step 160, the makeover program may select a layer for the makeover item. At step 170, the makeover program may apply the layer to the image, using methods known to those of skill in the art. The layer or layers may be established for the image during preprocessing step 110, or may be created as needed in one or more embodiments of the invention. The use of layers allows the makeover program to operate in an event-driven, order neutral fashion that provides a more pleasant and creative experience for the user. Thus, any makeover item may be applied to the image in any order. For example, the user may apply blush to the image, and then later add foundation. In a real-world makeover, foundation would be applied to the face before blush, and thus blush would appear "over" the foundation. The virtual makeover program allows the user to make changes to the makeover image in any order, easily creating the effect of correctly applying the products in a natural, real world order by segregating blush and foundation into separate layers, and then applying the layers to the image in the natural order, at step 170, for the user to view the effect.

When the user concludes the virtual makeover session, an option may be presented for the user to save the makeover image. At step 180, the makeover program may confirm that the makeover is complete. If so, at step 190 the layers may be merged into a single image for storage in one or more embodiments of the invention. This process may happen each time a makeover item is applied, each time the user changes Makeover Item Editors, or only before the final image is saved, as desired in various embodiments of the invention. The final image may be displayed to the user and stored, if so desired, at step 195. If the user wishes to apply another editor to the image, the process may resume at step 120, or save and exit at step 199.

Acquiring Image Data

As described above, an image or portrait in the spirit of the invention may include a digital or scanned photograph, a cartoon, drawing, avatar or other representation of a subject and in some cases a line drawing or other type of image. The subject of a portrait in the spirit of the invention need not be human, but may be an animal, or fantasy avatar, or other image to which the user wishes to perform sophisticated appearance editing.

Portraits to be input to the makeover program are typically digital images, though they may also be captured on film, video, or other physical media and later digitized by means well known to those of skill in the art. Digital images for makeover may be created or captured using an image capture device such as a digital camera, computer web camera, scanner or mobile phone camera. In various embodiments images may be captured directly into the makeover program, or load into the makeover program from a file. In a kiosk embodiment, the device may contain a camera to capture the image on the spot. Where the image or portrait is a cartoon, drawing, avatar or other non-photograph, the data may be converted into a form common for processing by graphic image program, such as, for example, formats such as .bmp, .jpg, .gif, .tif, .pdf or other well known computer graphic file formats. From whatever source or form available, the image may be input or uploaded and provided as a digital image data into the virtual makeover system for pre-processing.

Once received, the image data may then be stored on a server, on a client system, or elsewhere as understood by those of skill in the art. One or more embodiments of the makeover program will preserve the original and final images for subsequent presentation to the user, for use in the sharing and gifting functions, for scoring and/or gallery presentation where permitted, and for additional later revision by the user. Where the makeover program is implemented as a web based program, users may upload an image to the system for editing. Where the makeover program is installed on a consumer's computer, the makeover program may accept an image from a scanner or a file, or where the makeover program is installed on a commercial kiosk, the image by be inserted into the machine, or a photograph taken by the machine, and the resulting image may be printed but may or may not be stored for recall. Thus, any methods known in the art for obtaining and preserving digital images are within the scope of input for one or more embodiments of the present invention.

Image Preprocessing

Figure 2:
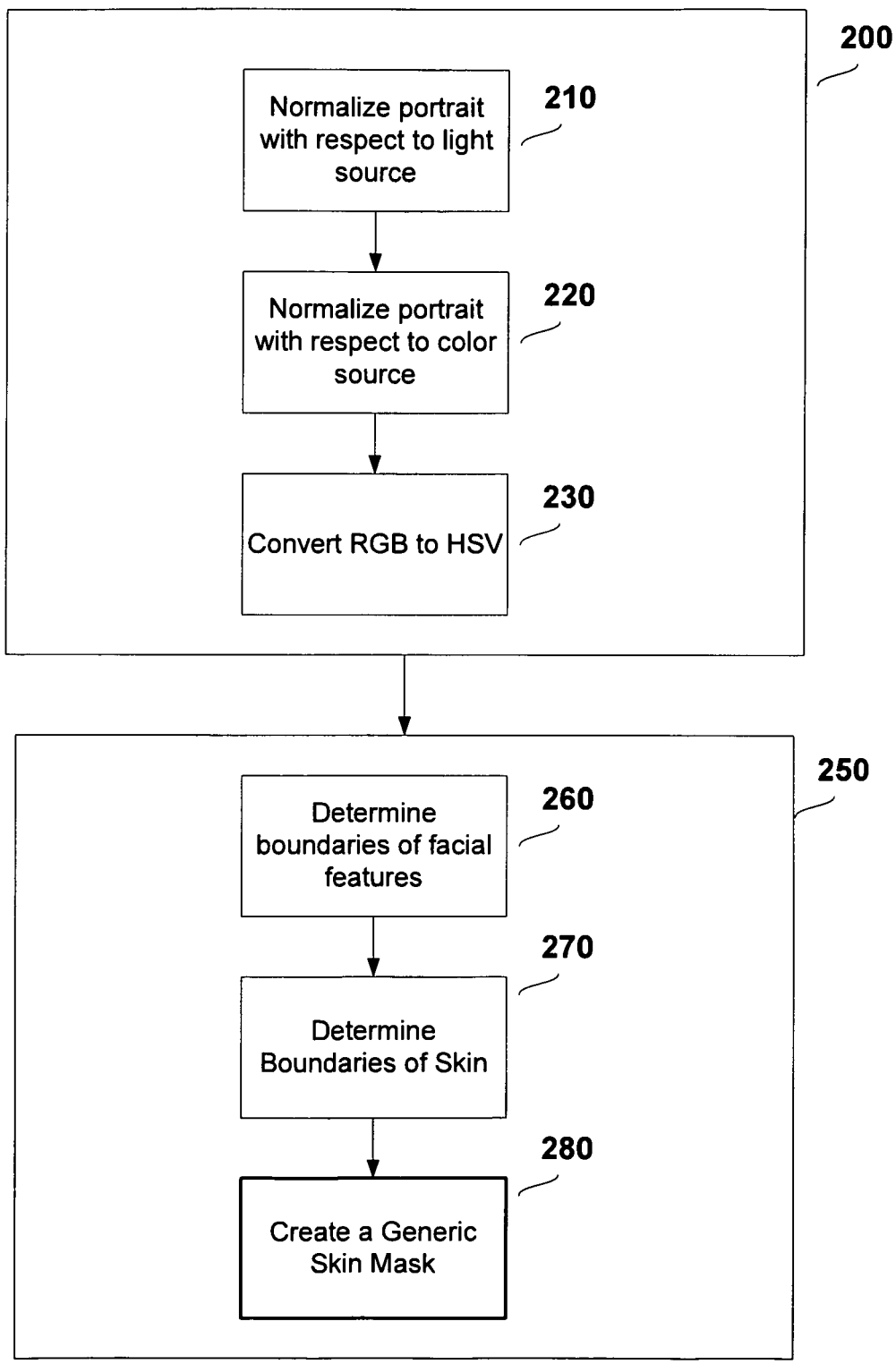
FIG. 2 illustrates various image preprocessing methods of one or more embodiments of the invention.

An optional preprocessing step of the makeover program of the invention is to improve the realism of the resulting makeover by detecting and correcting for less than ideal lighting and coloring in a portrait, as well as adjusting lighting and coloring of the portrait to correspond to that of prepared images of accessories, or alternatively to adjust the color and lighting of the accessories to best correspond to accurate color and lighting of various makeover items. Additionally, the makeover program may detect when the face in the portrait is not oriented to look directly into to the camera. Faces oriented at an angle to the camera present a challenge to producing a lifelike makeover, unless the skin mask, hairstyles, accessories and other items can be correspondingly adjusted by the makeover program to account for this altered facial orientation. FIG. 2 illustrates various image preprocessing methods of one or more embodiments of the invention. Preliminary preprocessing stage 200 includes light, color and other forms of image normalization. Various methods for each of these normalization embodiments are described below.

FIG. 2 also illustrates a second preprocessing step, where the input image may be evaluated to determine information regarding the pixel boundaries of various facial features within the portrait. Preprocessing stage 250 represents one or more types of facial evaluation that may be performed by one or more embodiments of the invention. Before the makeover program of the invention may create and apply one or more layers of lifelike and photorealistic makeover items, the makeover program may acquire input regarding, for example, which pixels of the image are of the lips, which are of skin, and which are of eyes? Various methods for determining facial feature boundaries are described below. In one or more embodiments, the makeover program may automatically detect the facial feature boundaries. In other embodiments, the user may be provided guides to easily delineate the pixels for the makeover program. In still other embodiments, these methods may be combined for one or more editor functions of the makeover program. Facial detection and facial feature detection are also described below.

Light Detection in a Portrait

The makeover program of one or more embodiments of the invention may analyze the portrait to determine the color, direction and/or brightness of the light as seen in the portrait. One or more embodiments may normalize the portrait with respect to the light source color, light direction and brightness associated with the portrait at steps 210 and 220. This may be done as an automatic or semi-automatic process.

The normalized portrait image allows for the application of cosmetics, styles and accessories that may be independent of the brightness, light color or light direction associated with the original portrait. Other embodiments may blend cosmetics, styles and accessories as captured from different light directions and colors onto a portrait to maintain the original shading, light color and light direction.

Color Detection in a Portrait

The color normalization and detection function 220 may be configured to detect skin tone and light color and direction associated with the face in the portrait. In one or more embodiments, the color detection function may be configured to eliminate shading associated with said face to improve the accuracy of color detection. The color detection function may be configured to build a color model associated with facial skin tone alone, or may also consider eye color, lip color or any other facial feature color that may impact the overall color impression of the face. The color model permits the makeover program to suggest makeover item colors that will flatter the face in the portrait. The color detection function may be configured to detect light color based on reflected highlights on the face in a portrait based on the dichromatic reflectance model. These models are well known to those of ordinary skill in the image processing arts, and so will not be described here in detail in order to avoid obscuring the invention. Any other reflection model or algorithm may be used as long as it may be capable of detecting the light color. The color detection function may be configured to classify said skin tone into a skin tone classification and may use the light color to color correct the color model of the skin for example. For the purposes of understanding these prior art models, the paper: "A Framework for Realistic Image Synthesis," by Donald P. Greenberg, et al around 1997, Program of Computer Graphics, Cornell University, is hereby incorporated by reference.

Converting RGB Input to an HSV Model

The challenge of using only a pre-defined (generic) skin color model for rendering the face in the portrait includes that variation of lighting conditions, range of skin coloration among subjects, camera hardware settings may create a great deal of variation and complication to prevent the makeover program from determining acceptable skin colors for producing preferred product recommendations.

The makeover program of the invention may use an adaptive skin color model, which may be created by one or more embodiments of the makeover program using one or more of the following methods. In a first method, the makeover program may handle variation in lighting brightness by separating color (chrominance) from brightness (luminance) and in particular using the Hue Saturation Value ("HSV") color space. Therefore, a precursor step may be to convert a portrait image from a Red-Green-Blue ("RGB") model to an HSV model. At step 230, the makeover program may convert RGB data to the HSV model. The makeover program may perform color-based skin classification using Hue (H) and Saturation (S), since the Value (V) carries the brightness information of the lighting that may not be useful for classification. Other color spaces that decompose color into chromaticity and luminance may be used such as the Hue Saturation Luminance color space. The makeover program may model generic color distributions using a single Gaussian distribution and the colors for a particular face as a Gaussian mixture model (GMM) with a plurality of Gaussian components.

A second method may comprise a step whereby the makeover program may estimate from a comprehensive training set the parameters (mean vector and covariance matrix) of a bivariate Gaussian distribution, and use this as a generic skin color model. Other generative statistical models may be used to capture the distribution of skin colors in one or more embodiments of the invention.

Facial Feature Boundaries Identification/Detection

In one or more alternative embodiments, preprocessing may include the user being provided with lines and a plurality of drag-and-drop control points to provide the makeover program with detailed boundary information for various facial features. Step 260 of FIG. 2 indicates the step of determining the boundaries of facial features as part of the preprocessing of a portrait image. One method for the user to provide boundary information is to adjust program provided "control points" to indicate the boundaries. Various methods of placing and controlling such points are known in the art. For example, control points connected by boundary lines may be presented near the eye, and the user asked to drag the points to, for example, the outer and inner corner of the eye. In doing so, the user will adjust and stretch the boundary lines that will define for the makeover program the pixels constituting the eye, for example. In one or more embodiments the boundary lines look and feel like "rubber bands" to provide the user a familiar, easy to understand and comfortable set of controls. The boundary curve defined by the control may be defined by a polygon or a spline such as a Bezier spline, B-spline, Lagrange spline or non-rational uniform B-spline (NURB).

In one or more embodiments, the system may detect or calculate positions for areas (or "facial features") of a face in a portrait, for example, the boundaries of skin, eyes, mouth and hair. Calculated positions may be used in place of, or in conjunction with, points provided by the user to determine the boundaries of the various facial features. The system may use the calculated positions to enable photorealistic application and adjustment of virtual cosmetics, styles and accessories at the correct locations within a portrait. A portrait, as used herein, means a headshot photograph, digital image, streaming video image, animation, avatar or artistic rendering or other image of a person's face. For example, in one or more embodiments of the invention, the hair color and skin tone may be blended at the top of the forehead to prevent a "cutout" appearance at the boundary between the replacement hair and the skin.

The facial features boundary detection function may be configured in one or more embodiments to detect the pixel boundaries of a face in a portrait. The facial feature boundary detection function may use the Viola-Jones face detection algorithm, that can be found in the International Journal of Computer Vision, 2004, or any other pixel delineation algorithm known to those of ordinary skill in the art capable of detecting the boundaries of a face in a portrait may also be used by one or more embodiments of the makeover program.

The facial feature boundary detection function may also be expanded to detect other facial features such as skin, hair, eyes and mouth boundaries within the facial boundaries. The detection of such additional facial features may be performed automatically using a Taylor-Cootes active appearance model and fitting algorithm for face-feature detection. However, any other algorithm capable of detecting the boundaries of these additional facial features may also be used by various embodiments of the invention. In the event that an automatic face detection or face feature detection fails, or in some embodiments in addition to the automatic detection or in place of it, a user may use computer interface to indicate the locations and shape of the face and face features using control points, described elsewhere herein. This may be done using a graphical user interface (GUI) that may allow the user to adjust the locations of automatically detected face and face feature locations and shape to a more precise location.

Precise placement of the facial and facial features boundaries allows a better match between makeover items and the underlying portrait. When used together, as a user sequentially provides adjustments to features, estimates of the locations and shape of other features may be automatically re-estimated, providing a hybrid or "semi-automatic" detection of facial feature location, placement and orientation. For example, adjusting the shape of the left eye may lead to an adjustment of the shape of the right eye automatically by the makeover program. For each control point or adjustment that a user makes, that selection informs the initial estimate provided to a user for subsequent input and it may control the zoom and center of the window of the user interface. For example, consider the process in order of segmenting out the left eye, left iris/pupil, right eye, and right pupil. After the user has specified the shape of the left eye and iris position, the makeover program may predict the shape and location of the right eye (the shape may be reflected bilaterally about the center of the face). After the left iris and pupil are defined, the right iris and pupil should be about the same size. The position of the iris in the right eye should be about the same (not reflected) as in the left eye.

Detection of Skin Boundaries and Creation of a Skin Mask

Next, the makeover program may use the detected facial features to align a generic 2D binary mask over the image to identify pixels in the image that are candidate pixels to be labeled as skin. This is illustrated in the preprocessing flow as steps 270 and 280. The mask may be a generic facemask capturing typical locations of human skin. A transformation may be estimated to align the generic 2D binary mask with the face image. An affine transformation containing six parameters maybe used for geometric alignment. An affine transformation preserves the collinearity (i.e., all points lying on a line initially remain on the line after the transformation), the ratios of distances along the line, and parallelism.

Figure 3:
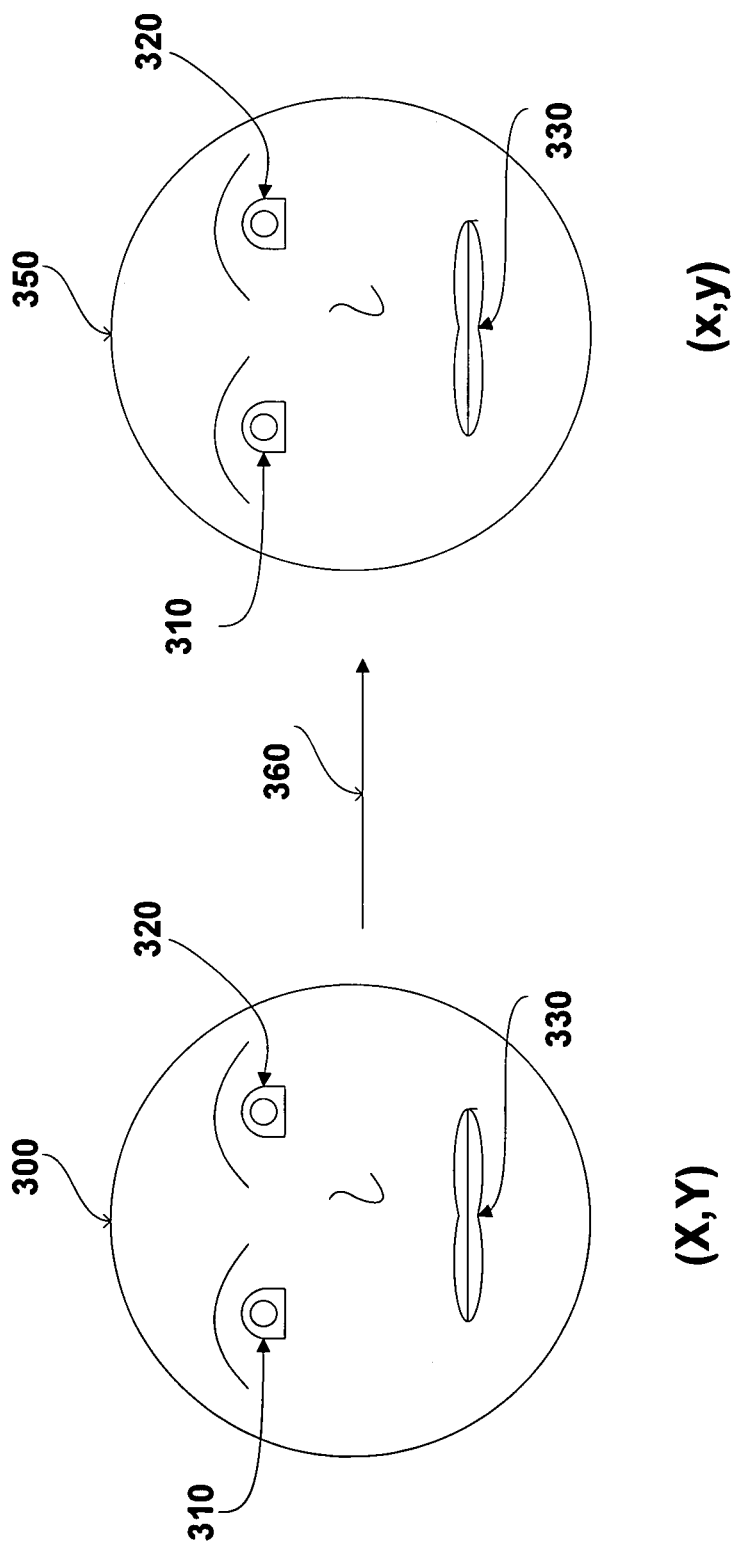
FIG. 3 illustrates a transformation a generic 2D facemask to a uploaded portrait using six (6) affine transformation parameters in one or more embodiments of the invention.

FIG. 3 illustrates a generic 2D facemask being aligned to the uploaded photo of an actual face using six (6) affine transformation parameters, using facial features 310, 320 and 330, each on generic facemask 300 and portrait face image 350, where 310 and 320 represent points for the right and left eyes, and 330 represents a point on the lips on each face, respectively. Equation 1 is used to calculate the six parameters of the affine transformation 360 from generic facemask 300 to portrait image 350. After applying the transformation, the generic facemask may be overlaid on the portrait to approximately locate the face region in the image.

$$X = ax + by + c$$

$$Y = cx + dy + f \qquad \text{Equation 1:}$$

from (x,y) to (X,Y)

The masked skin region may contain pixels that are a mixture of skin and non-skin, such as hair, glasses, background, and eyebrows. The mask may also already have cut-outs determined for the face's eyes, eyebrows, mouth and other features.

Next, the makeover program may classify the pixels within the masked region of the image as "skin similar" using a generic skin color model (Gaussian) that was learned offline. In preferred embodiments, the makeover program may choose a conservative threshold to minimize the number of false negatives, such as mislabels of pixels that are of true skin but are labeled as non-skin. The resulting set will contain pixels that are both skin and non-skin, but the vast majority of pixels will be skin colored.

A probability distribution of the colors of the "skin similar" pixels is then estimated. The makeover program may use a Gaussian mixture model (GMM) with two Gaussians and Expectation Maximization (EM) algorithm to learn the GMM parameters, but other algorithms could be used. The makeover program may consider one of the Gaussians to be dominant (the one with larger weight), and it is taken to capture the true skin color while the other captures the color of the non-skin pixels. Using the learned GMM, the makeover program may perform a second classification on the skin-similar pixels to produce the output that is comprised of those pixels in the image that are determined to be skin.

Since the makeover program has available the locations of points on the eyes and mouth, from the process above either from user input or automatic detection or both, the makeover program may then identify a region of the portrait that may be inside the face and is likely to be composed almost entirely of pixels that represent areas of skin. The makeover program may use a rectangular region defined by areas below the eyes and above the mouth, and lines descending from the outer corner of the left eye and the outer corner of the right eye, to make this identification. This area may be identified as a Training Region.

The makeover program may then "learn" the mean and covariance of a Gaussian model of the colors (HS) of pixels within the Training Region. Next, for each pixel in this masked region, the makeover program may calculate the probability that a pixel is skin using the learned Gaussian parameters. Next, the makeover program may select a threshold so that by applying a Gaussian distribution, a fixed percentage of pixels (for example, 95%) of the pixels in the Training Region may be labeled as skin pixels. Next, the makeover program may classify the Mask Region as skin pixels and non-skin pixels using the calculated probability and the threshold computed above by "thresholding" the probabilities. Finally, some parts of the skin may be falsely classified as non-skin pixels because of strong lighting, specularity of the surface, highlights, or saturations on areas such as the forehead, nose tip or chin. As used here, "specularity" refers to a mirror-like reflection or glossiness of surface resulting in highlights. On a face, this might be seen as the glint in an eye, the shine on an oily nose, or the reflection of a metallic or plastic eyeglasses frame.

The makeover program may re-inspect the V values (in HSV color space) of pixels in these regions. If V values are above some thresholds, the makeover program may determine that those pixels are saturated, and reclassify them as skin pixels.

Makeover Editors

Creation and modification of makeovers may be performed using a computer particularly programmed to perform the methods described here, using at least one of makeover editor. Available makeover items may be divided into a number of specialized groups to facilitate use in editing particular parts of a portrait. These groups may be collected into particularized editors that provide a convenient user interface for interacting with particular kinds of makeover items. In one or more embodiments, the makeover program may provide skin, eye, mouth, hair and accessory editors. Skin makeover editing may include makeover items such as foundation, concealer, and blush. Eye makeover editing may be performed through the application of makeover items such as eye shadow, eyeliner, mascara, and colored contact lens. Mouth makeover editing may be performed through the application of makeover items such as lipstick, lip liner, lip-gloss, lip plumping and teeth whitening and straightening. Sophisticated hairstyle makeover editing may be performed by the makeover program through the application of makeover items such as a hairstyle, hair color, and hair accessories. In one or more embodiments, the makeover program may provide controls to allow the user to shape the hairstyle to the head in the portrait. Accessory makeover editing may be performed through the application of accessory makeover items to the portrait. Accessories may include items such as eyeglasses, jewelry, clothing such as hats, headbands, or hair clips, as well as tattoos and piercings. Accessory editing may comprise size adjustments, rotation, color changes, or placement location of various accessories available to the makeover program through a library of accessory photographs. Makeover editors present options for the placement of makeover items particularly calculated to the item type. For example, various elements such as for example blush, may be positioned based on calculated locations on the portrait, and then rendered on the image by one or more embodiments of the invention in a photorealistic manner in a style selected by the user.

Figure 4:
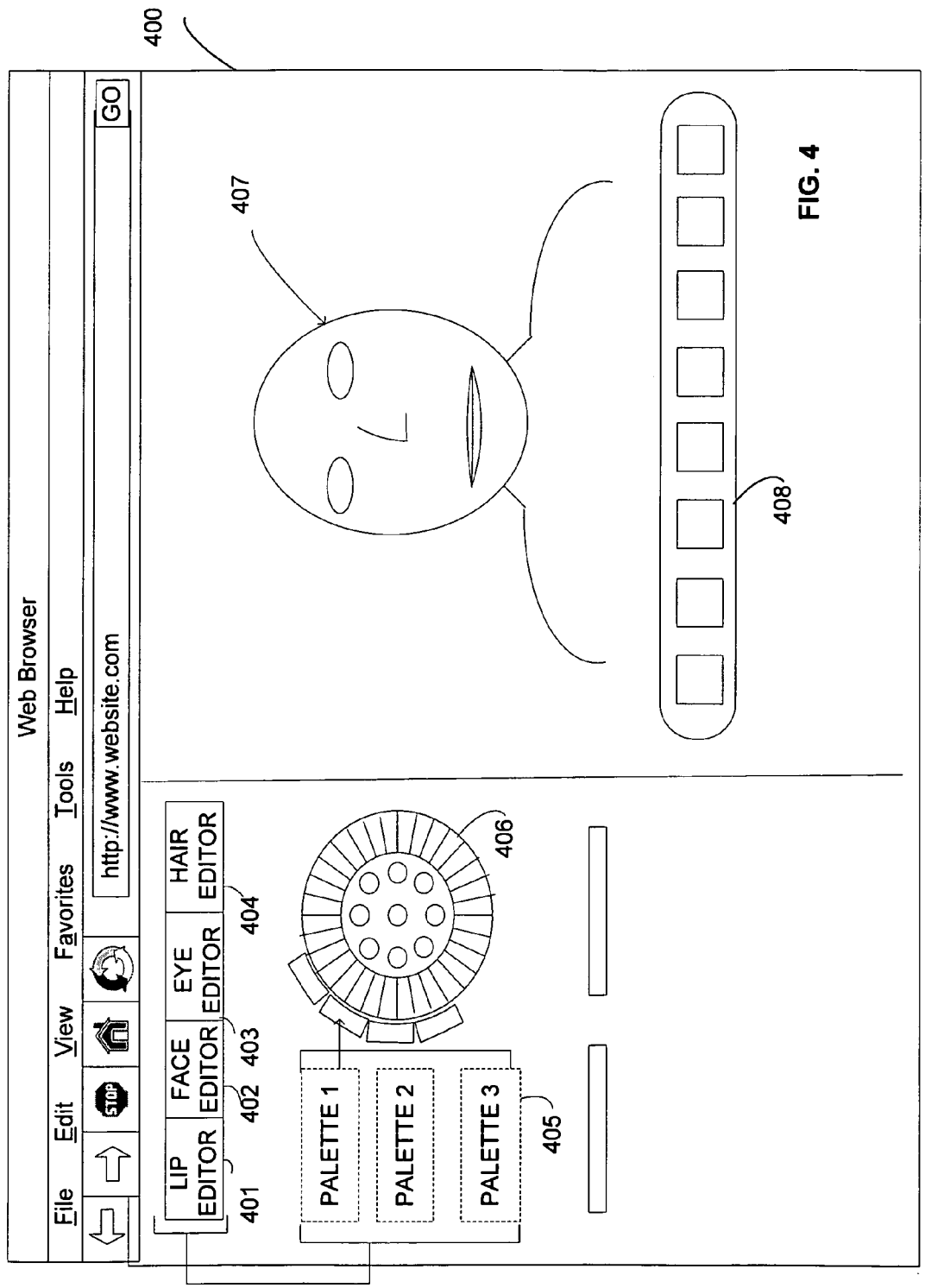
FIG. 4 illustrates a storyboard of a Graphical User Interface providing various Makeover Editors in one or more embodiments of the invention.

FIG. 4 illustrates a storyboard of a Graphical User Interface providing access to various Makeover Editors in one or more embodiments of the invention. FIG. 4 provides an exemplary user interface 400 displaying four exemplary Tabs, shown as Makeover Editor Tabs 401-404. More detail on graphical user interfaces available to implement one or more embodiments of the makeover program may be found in U.S. Provisional Application 61/037,319, incorporated by reference elsewhere herein. The exemplary interface 400 illustrates a display showing portrait 407, available for editing, a program navigation bar 408, a set of makeover item palettes 405 and a color wheel 406. The makeover palettes may be restricted based on the editor selected. For example, if Lip Editor 401 is selected, makeover item palettes 405 may comprise Lipstick, Lip Liner and Lip Gloss palettes as palettes 1, 2 and 3. Color wheel 406 may comprise colors available for the current selected palette 405. While the exemplary interface displayed in FIG. 4 executes in a web browser, the makeover program of the invention is not so limited, and may run as a stand-alone application, a mobile application, or in any other format available to user as will be easily understood by those of ordinary skill in the art.

The makeover editor function(s) of the invention may be configured to provide a makeover item to apply with respect to the portrait in one or more embodiments of the invention. In one or more embodiments, at least one makeover editor may be configured to provide the makeover item based on other makeover images. In some embodiments, the invention may restrict such import to images where the subjects of the source and destination portraits have similar facial characteristics, for example skin tone.

Looks associated with other portraits exhibiting the same basic face shape or skin tone may be presented to the user to allow for quick selection of recommended looks. Makeovers may be assigned popularity values, and the most popular makeovers may be presented by the system for example. Popularity values may come from voting by other users, by experts, by highest hit counts or other statistical methods. Popular makeovers may be filtered to present only those makeovers that may be applicable to the user based on a portrait of the user. In addition, celebrity looks may be presented to allow for the selection of the look of a celebrity.

At least one makeover editor function may be configured to allow a second user to edit a look in conjunction with another user. In one or more embodiments, a model-view-controller design pattern may be used to allow user events to be captured by the system to keep both views on displays 720 and 730 in synchronization. Any other method that may be capable of allowing two or multiple users to edit a look together may be in keeping with the spirit of the invention including screen sharing or whiteboard software programs.

Makeover Editor Examples

FIG. 4 illustrates a storyboard of a Graphical User Interface providing various Makeover Editors of an exemplary embodiment of a makeover editor for editing skin appearance by applying foundation. In addition, FIG. 4 shows tabs for accessing face makeover editor 402 and for applying foundation, blush, and concealer to the face. Tab 401 allows the user to edit lip color, shine, plumpness, lip liner and similar makeover items. Tab 403, the Eye Editor, allows the user to apply makeover items such as eye shadow, eyeliner, mascara and colored contact lens. Tab 404, the Hair Editor, allows a user to select a hairstyle, color, length, highlights, low lights, and other adjustments to hair. The Hair Editor is covered in more detail later in this description.

Various embodiments of the makeover program of the invention may provide one or more makeover editor interfaces for the user to select and apply makeover items to the portrait. Makeover editors may contain functions such as: editing skin appearance by applying foundation and/or concealer; covering freckles or removing moles or blemishes, applying blush, eye shadow, eye liner, mascara, false eyelashes, color contact lenses, lip color, lip liner, lip gloss. Various embodiments may provide teeth whitener, teeth may also be straightened or veneers added in one or more embodiments of the invention, for example. Additional embodiments may provide accessories such as glasses.

The invention provides special facility for shaping a hairstyle from a library of hairstyles to conform to the areas of the portrait identified as areas accepting hair. A hairstyle may be selected, and then the user or the makeover program may warp the style to fit the face properly to produce a photorealistic effect. The hair may be applied at the areas detected by the automatic detection function typically around the face, and may be color blended with the border of the skin to avoid a cutout look. In addition, the hairstyle may be rotated using a rotate button to match the in-plane rotation of the face as detected in the portrait in one or more embodiments of the invention.

Image Warping

Image warping may be understood to be the process of digitally modifying an image to alter the shapes portrayed in the image. A warp may further be delineated as a forward warp or a reverse warp. A forward warp may be represented by a pair of functions that map each location (x,y) in a source image to a related location (x',y') a destination image. Predictably, a reverse warp may map the location (x',y') in a destination image to a location (x,y) in a source image. There are several ways that an image may be warped using a given warping function. For example, in using a reverse warp, the color at pixel (x',y') of the destination image may be calculated by interpolating the value of color at the pixels immediately surrounding location (x,y) of the source image.

Recommendation Engine

The makeover program also may provide the user with recommendations for color, styles and shapes that will provide a lifelike and photorealistic result to the makeover image. One or more methods for making product recommendations to the user are detailed below.

In summary, to determine recommendations based on a learned approach, the face attributes such as skin tone, eye color, hair color, face shape (which includes the contour of the face, the distances between various face parts, the shape of the forehead, jaw bones, chin for example), eye shape, nose shape, and mouth shape may be determined using methods described elsewhere herein. Using these attributes, the makeover program may select information stored for faces with similar attributes, and recommend products selected by those similar users. This learned approach may include considerations based on similar skin tone. Similarity of skin tone may be determined by transforming the user's skin color into the HSV space, as described above, and learn the user's skin tone from the adaptive skin-color-model learning module. Based on the skin tone and popularity of products used by user with similar skin tone, products such as foundation may be recommended to the user.

Eye shadow and eyeliner may be recommended using a similar approach based on selections by other users with similar skin tone, eye and hair color and face shape, eye shape, for example. In some embodiments, particular eye shadows may be recommended based on the shape of the eyes and eye region. For example, some eye shadows and mascara may be used on small eyes to make them look bigger, while for bigger eyes certain makeup will make the eyes shape more attractive. Makeup techniques are well known to those of ordinary skill in the makeup arts and as such are not detailed here.

Prior similar user selections may also be used as weights in the learning function of the recommendation engine in one or more embodiments of the invention. Recommendations of hairstyles and eyeglass styles, for example, may be similarly determined based the makeover program's analysis of the face shape as determined from the 2D or 3D face model as described herein. Users with similar face shapes may have similar PCA coefficients for building the shape, and thus produce similar recommendations.

In detail, a recommendation engine in keeping with the spirit of the makeover program may include one or more of the following capabilities: recommending specific products or attributes of products (color, gloss, matte) in a specific category, such as lipstick, eyeliner, blush, glasses, sunglasses, and such. First, an application style for a particular product category such as placing blush high on the cheekbones may be recommended. Second, the engine may recommend hairstyle and hair color. Third, the engine may recommend a "look," as defined here and which may include a combination of products, styles of application, and hairstyle and hair color. A recommendation engine in the spirit of the invention may make the following types of recommendations. This list is exemplary and not a limitation on the scope of the invention. Recommendations may be created using expert system approaches, or other techniques known to those of skill in the art. Recommended items may be selected based on well known principles of the makeup arts, as well as possible weighting to user preferences, advertiser commitments, and other aesthetic and commercial considerations as will be understood by those of skill in the art.

For example, a product or a combination of products that is well matched on aesthetic grounds, or from the same product line, may be recommended together. Recommendations may span many areas of expertise and marketing. For example:
 a user's facial attributes (such as shape and color);
 a user preferences (for example, a preference for organic versus non-organic products, expressed color preferences, expressed brand preferences);
 the placement of makeup (for example, people with non-prominent cheek bones may want to make them prominent using a particular placement and style of blush); and
 the amount of makeup—based on ethnicity or other factors the recommendation engine may recommend the amount of makeup to be applied (for example, those with darker skin tones may prefer to wear more intense makeup than those of lighter coloring).

The recommendation engine may take as input one or more of the following data: facial attributes derived from portrait images; colors such as eye color or skin color; user attributes; and user preferences. Facial attributes may include skin color, eye color, eyebrow color, hair color, facial hair color, face shape, face symmetry, facial irregularities (moles and scars, for example), distance between various face parts, eye shape, ear shape and size, nose shape, nose width, nose length, lip thickness, mouth width, teeth color, shape of the jaw line, shape of the forehead, and the output of a set of image filters placed at determined locations on the face. Colors may include eye color or skin color, and may be represented in one or more embodiments as:
 a single color in some color space;
 a histogram; and
 a parameterized probability distribution such as a Gaussian with its mean and covariance.

User attributes may include: personal characteristics of user provided or may be obtained from a database, and include but may not be limited to: age, weight, height, gender, skin type (for example, oily, dry, flakey, normal, acne), hair type (curly, kinky, dry, straight, and thin), and natural hair color. User Preferences may include: general preferences and preferences for the recommendation type that may include: cost preferences, organic/natural products, high SPF rating, brand preferences, a "club" look, a "professional" look, looks seen on a "top ten" list, looks featured in a magazine, or others. Some user preferences may be treated as hard preferences, such as a preference for organic products. Others preferences may be "soft," such as a preference for cheaper products over more expensive ones, or such as "all things being equal" a preference for natural products. The recommendation engine takes the face attributes, the user attributes and the user preferences as input, and outputs a set of recommendations of the above four types.

Three Exemplary Sources of Recommendations

The following section provides three exemplary sources of recommendations to be provided to the user regarding products available in the virtual makeover program for application to the portrait. One or more embodiments of the invention may use any or all of these sources, or provide an embodiment of the invention that does not provide a recommendation at all.

In one or more embodiments of the invention, the following are three examples of methods that may be used to select products to recommend to users of the virtual makeover program. These three recommendation source examples comprise: expert recommendations, facial attribute recommendations, and scored gallery recommendations. The recommendation methods of the invention are not limited to these three sources, which are provided as examples only. Those of skill in the art will recognize that various combinations, as well as other similar sources, fall within the scope of the invention as described here.

Expert Recommendations

Expert recommendations may comprise one or more experts who provide general recommendations for various products, styles, colors, and techniques in different combinations to be associated with various facial attributes and user preferences. Expert recommendations may be captured as rule-based data comprising a set of preconditions key to either facial attributes, user preferences, or a combination thereof. Where a user satisfies one or more preconditions, the recommendation process will present the user with the recommendation on request. The preconditions may consider only a limited set of facial attributes—for example, a recommendation on hairstyle may consider only face shape but not skin color or eye color, for example. If a user's facial attributes and/or preferences do not satisfy all preconditions of any rule, the rule that satisfies the most preconditions may be triggered. In one or more embodiments, the recommendation method may present an ordered list of recommended products, where the highest-ranking products are selected when user facial attributes and/or user preferences (such as for organic products) trigger recommendation rules.

Facial Attribute Recommendations

In one or more embodiments recommendations may be based on the portrait's facial attributes. The makeover program may have a very large set of examples of makeovers done by other users available for evaluation. In one or more embodiments, a stored makeover may contain the original portrait image as well as the products and styles chosen by the user. From this stored makeover data, the makeover program may derive the face and user attributes using skills known to those in the art as well as facial feature detection methods described herein. As the stored data grows over time these selections may comprise a large volume of data regarding the user community's preferences for styles, products, and color combinations, for example. Identifying preferred choices for similar facial attributes and offering them as recommendations, the makeover program provides the user with the community's collected knowledge, sense of fashion, style, and good taste.

In one or more embodiments, the makeover program may treat the facial attribute and user choice data as training data for a learning engine. For example, given particular set of one or more facial attributes, the learning engine may select all recommendations for faces that display a matching set of attributes. One or more alternative embodiments may return all faces that have at least a certain number of similar attributes (for example, all faces that have at least 8 out of 10 tracked attributes). Whatever the criteria, the makeover program may produce a collection of recommendations. The resulting makeover selections may then be ranked by, for example: (A) the number of times in the training data where this recommendation was selected (thus, "among all the users that look like me, what is the most popular recommendation,") or (B) the degree to which the selected makeovers correspond to other user preferences, or (C) a combination of popularity and degree to which the selections correspond to prior user preferences.

Scored Gallery Recommendations

A third option for selecting other makeovers as a recommendation to the user of the makeover program may comprise using a "scored gallery" of prior makeovers, where the makeovers are "scored" by the public (other users of the makeover program.) Makeovers with high ratings may be presumed to be preferable by the community, and the individual components (products, application styles, hairstyles) may be presumed to be good choices for portraits with similar characteristics to those of the faces in the gallery. The following three-step recommendation method may be understood from this observation. One or more embodiments of the makeover program may implement this three-step procedure as a scored gallery recommendation method.

First, given a set of facial attributes, a set of makeovers in the gallery may be selected where the subject has similar attributes (as in the Facial Attribute recommendation method, the matching criteria may require an exact match of all attributes or may allow an exact match of limited number of attributes, or it might be programmed to select the top X closest matches). Second, given this result set, the makeovers selected may then ranked by: (A) the score of the makeover in the gallery (the top scoring look in the gallery for similar facial attributes may be highest ranked); (B) the degree to which the recommendation will satisfy the user's stated preferences; or (C) a combination of the gallery score and degree to which the recommendation will satisfy the user's preferences. Third, the result of the above process may be a collection of makeovers.

The recommendation that results from the above selection process may take the form of a recommended product, application style or technique, hairstyle or color, a location to buy the product (whether a physical location or online store), or a look that may be in the makeover. The final recommendation may be either the top ranked recommendation or the user may choose from an ordered set. Once selected, a recommended makeover may be applied to a given portrait using techniques similar to those of applying a given look to multiple images.

Methods of Applying Makeover Items

Users may perform a makeover using the various makeover editors of the makeover program. Makeover editors in the nature of the invention are illustrated in FIG. 4, for example. Performing a makeover comprises a user selecting an Editor (associated with an area of the face to makeover, such as Lips Editor 401, for example.) Next, the user may select a Palette Group from Palette List 405. For example, the user may select Palette 1, which may represent lipstick. Color wheel 406 may then display lipstick colors for application to portrait 407. In order for the makeover program to apply a selected lipstick color to the lips of the face in portrait 407, the makeover program must have clearly delineated pixel boundaries for the lips. The makeover program of the invention may provide multiple methods for determining the pixel boundaries of the lips or other facial features to be edited with Editors 401-404, for example, which are discussed above under Image Preprocessing.

Apply Makeup and Hair Choices Via Layered Algorithm

Makeover Editors may be used to apply makeover items to individual graphic layers. When presented to the user, the layer may be displayed over the base image, properly sized, shaped and aligned using the methods of detection and masking described above, so that an appropriate photorealistic effect is achieved. When multiple layers are employed, each layer of makeover item(s) may be layered onto the newly formed image until the entire collection of layers has been added. Each Editor may add one or more layers above the base image, in predefined order, starting with the conceptually lowest layer, to produce a final makeover image.

Figure 6:
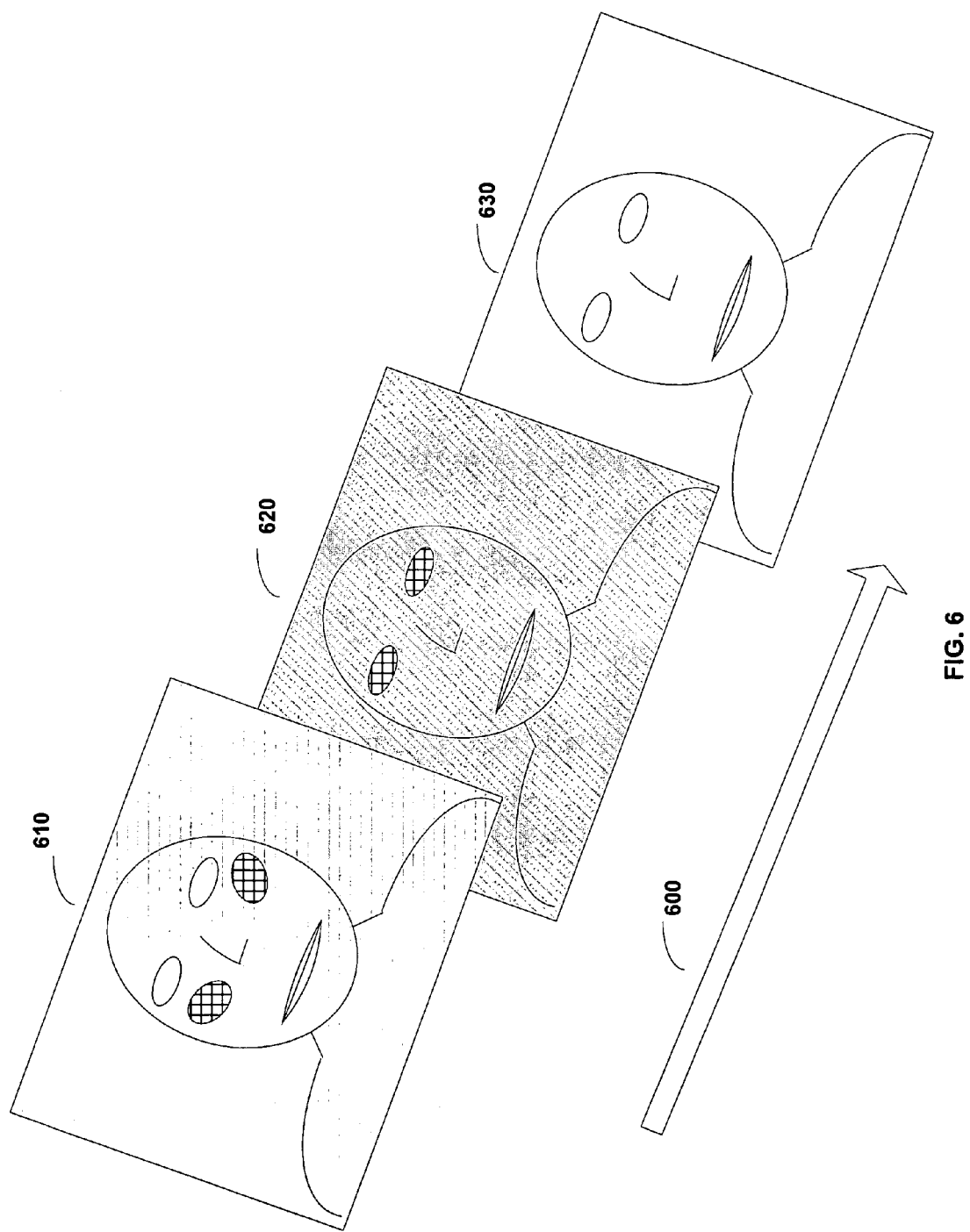
FIG. 6 illustrates a conceptual layering of makeover items onto a base image.

FIG. 6 illustrates a conceptual layering of makeover items in one or more embodiments of the makeover program. Arrow 600 indicates that the layers 610 and 620 are to be applied to base image 630 in a predefined order. In this conceptual example, layer 610 represents a Face layer where the user has defined a blush makeover item, and layer 620 represents an Eye layer where the user has applied eye shadow. Both layers may be rendered onto base image layer 630 through their individual and appropriate masks (not shown) to produce a final makeover image. When all layers are combined into their pre-defined order, the resulting image may be displayed as the final makeover image. In one or more embodiments, skin layers (foundation, bronzer, concealer, and blush, for example,) would be rendered as the lowest layers (applied first to the base image.) Lip layers, such as lip liner, lipstick, and lip gloss, may be applied in order. Eye layers, such as liner, shadow, and mascara, for example, may be applied before or after lip layers, as the two sets are conceptually independent. Hair and accessory layers may be applied last in one or more embodiments of the invention.

The collection of layers with the associated masks and their positions and the corresponding product parameters (color, transparency, luster, gloss, metal content, and flecks) together define a "look." A look, as the term is used herein, does not include the base image itself. A "look" may be saved to a disk or other storage device, both associated with and independent of a portrait. Thus, the look may be loaded and applied to an original image. The look may also be applied to a second image of the same person and this second image may then become the base image in the rendering process. For this to be effective, the underlying facial features from the original image must be brought into correspondence with the second image. This correspondence induces a transformation of the positions and shapes of masked regions. For example, the position of the eye shadow region from the first image must be positioned relative to the corresponding eye, and it may need to have its shape altered to account for a portrait's 3D orientation. The foundation and bronzer layers, for example, would use the automatically detected skin mask associated with the second image rather than the original. The subsequent layers may be transformed according to their correspondence to the original image.

Hair Makeover Editor—Use of Control Points to Adjust Hairstyle

Figure 5:
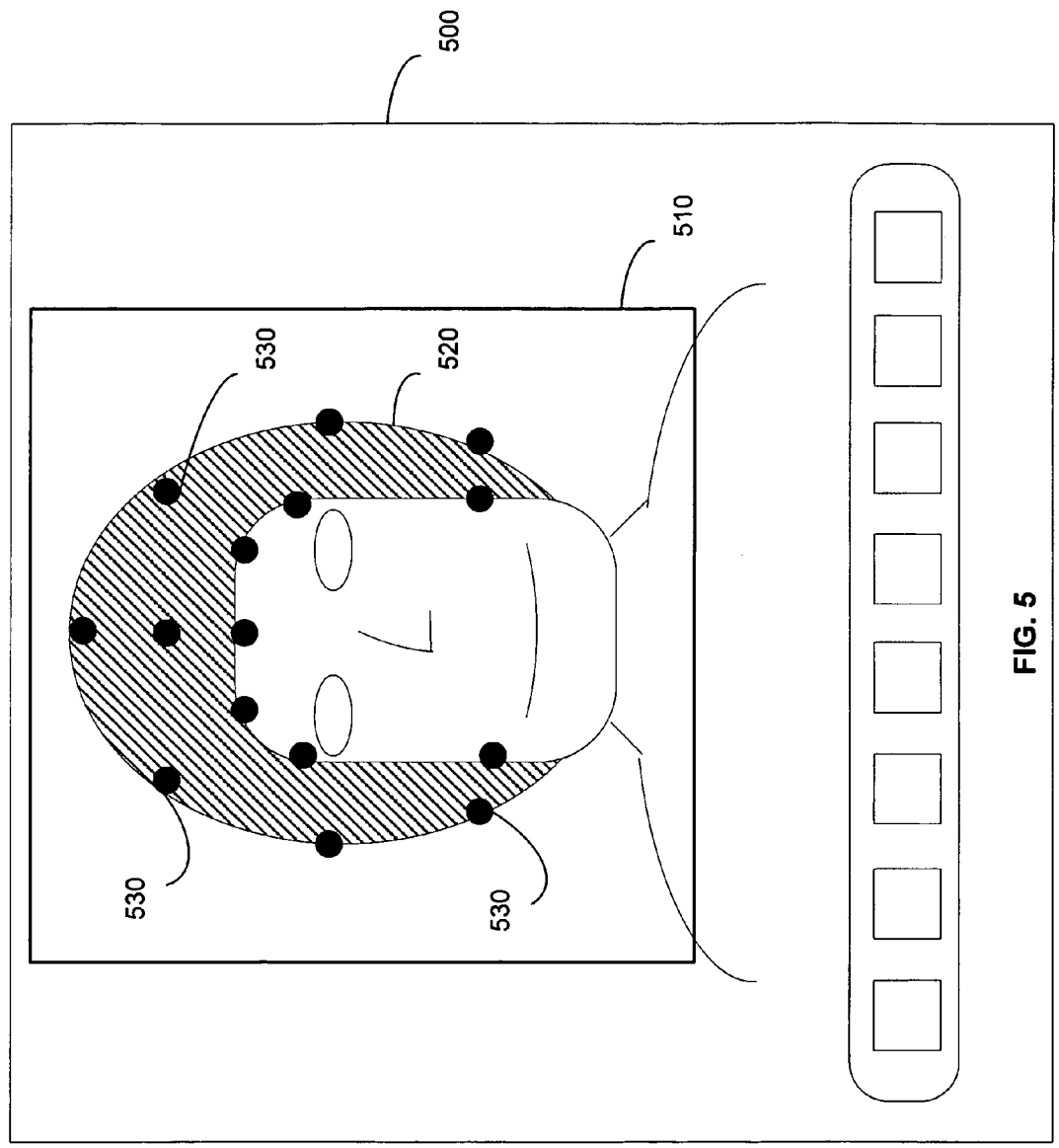
FIG. 5 illustrates a graphic user interface storyboard showing global and local control points for adjustments to hairstyle in one or more embodiments of the invention.

FIG. 5 illustrates a graphic user interface storyboard showing global and local control points for adjustments to hairstyle in one or more embodiments of the invention. This interface may be part of Tab 404 of FIG. 4, for example, or may be created as a separate interface in one or more embodiments of the invention. To create a lifelike placement of hair makeover items onto a portrait, the hair makeover item must "fit" the face in the portrait. To better create an appropriate fit, one or more embodiments of the invention may provide both local and global editing of hair makeover items, as discussed elsewhere herein. An exemplary embodiment of a makeover editor for editing hair appearance and placement by warping a hairstyle using control points is discussed later in this description.

FIG. 5 illustrates an example of the operation of placing, sizing and adjusting ("warping") hair makeover items in one or more embodiments of the makeover program. Screen 500 represents a user interface display or portion of a display. Hair overlay 520 may be adjusted by the user using either bounding box 510 or one or more control points 530.

In this example, bounding box 510 represents a form of global adjustment of hair overlay 520, while a plurality of control points 530 provide a local control of the hairstyle. To adjust the location of the hair on the head in one or more embodiments, the user may drag bounding box 510 in any direction to relocate the hair overlay on the portrait, providing global control. One type of global control may be to adjust the ratio of horizontal to vertical scaling of the hair overlay. This adjustment affects the entire hairstyle, and is referred to as a global transformation. Adjustments to translate, scale and rotate hair overlay 520 are other forms of global control that may be provided to the user. As used herein, the words "scale" and "resolution" are used interchangeably.

One type of global transformation is an affine transform, which may provide six degrees of freedom. In some embodiments, only translation and scaling functions, with three degrees of freedom, may be provided. Other systems may provide a full affine transformation, providing rotation and different scaling of x vs. y to provide two additional degrees of freedom. Other embodiments may provide less control.

A plurality of control points 530 may be used to acquire local control of the hairstyle. Adjusting any one control point 530 may allow the user to adjust the length, angle, fullness, length of bangs, and shape of the hair to fit the head, as well as orientation of the hair to the face in the portrait in one or more embodiments of the makeover program. Warping of the hairstyle may be achieved using affine warps of image triangles defined by a triangulation of the control points, thin plate spline techniques, or other splines defined by the control points.

Providing both global and local control of hairstyles may allow users to adjust the hairstyle in multiple ways, producing a more lifelike and photorealistic result. For example, with the controls described here, a user may lengthen a bang, extend a curl, or make the hair fuller, as well as get the hairstyle to fit more naturally around the face. When the hairstyle isn't properly located, shaped or placed for the face in the portrait, it often won't fit right when a global transformation is applied—there may be gaps between the hair and face, for example. With local control of the hairstyle, the user may achieve a more pleasing and lifelike fit of the hair to the head.

In one or more embodiments, the makeover program may provide a set of control points and use thin plate splines to allow the user to warp the hairstyle. When the control points are moved together in a manner that achieves global warps such as an affine transformation the user may create a more precise result. A user interface supporting the makeover program may include global controls to allow the user to translate, rotate, scale, shear, or change the aspect ratio (height to width) of the hairstyle. When a user desires to make a global change to the hairstyle, such as to translate, rotate, shear, or change the aspect ratio of the hairstyle, it is easier for the user to interact with a single user interface control rather than moving multiple individual control points to produce the desired effect. Such global controls may be implemented as an affine transformation of the hairstyle in one or more embodiments of the invention. When a user provides an input to move a given control point associated with a location on the hairstyle, the makeover program may translate, rotate, scale, shear or change the aspect ratio of the hairstyle, providing a simple user interface that produces a responsive and sophisticated result. All control points may be transformed by the makeover program using a corresponding affine transformation to move the control points resulting in a global warp of the hairstyle image with an intuitive and pleasing result displayed to the user. The user may apply global and local warps to the hairstyle in any order to achieve a precise and lifelike placement of the hairstyle on the portrait.

Portrait Analysis and Three Dimensional (3D) Face Models

Face May be Graphically Warped

One or more embodiments of the makeover program may import a digital image of a portrait as described herein. Next, the makeover program may create a 3D face model for use in face and feature detection as well as accessory placement. Embodiments of the makeover program may support portraits where the face does not look directly at the camera. The creation of a 3D model of the face allows the face to be graphically "warped" by the software. The term warped or warping may be used herein as in its common definition known to one of ordinary skill in the graphic arts, which may include but may be not limited to "a continuous deformation from one keyframe or 3D model to another. In 3D, this may be often achieved by approximating a surface with a triangular mesh that may be continuously deformed. In 2D, it may be generally performed by either distortion or deformation."

The portrait analysis function may take as input an image with a face and have available a 3D face model as well as a 3D accessory model. Various embodiments of the invention may use one or more types of 3D models to represent a face. One model may represent faces in general (an average face.) This is a rigid face model. Alternatively, or in addition, a 3D model may be a parameterized model where the parameters may be meaningful variables such as nose size, or may be coefficients of some basis function. A well-regarded parameterized model is the 3D morphable face model of Blanz and Vetter. See: "A Morphable Model for the Synthesis Of 3D Faces," Volker Blanz, Thomas Vetter, SIGGRAPH 1999, incorporated herein by reference (hereinafter "SIGGRAPH 1999").

The 3D morphable face model may be constructed offline from a data set of 3D faces along with texture or reflectance maps. Using principle component analysis (PCA), one or more embodiments may use average face shape and a set of principle components of variations in face shape. Likewise, PCA may be applied to texture maps to get an average texture and directions of texture variation.

The first step of algorithms implementing this method may take the image of a portrait and the 3D face model constructed offline, and use them to estimate the 3D position and orientation of the face relative to the camera that took the image, as well as the shape parameters of a parameterized model. For a rigid model, six pose parameters (three 3D translation and three 3D rotation parameters) may be estimated. For a morphable model, the shape parameters as well as the pose parameters may be estimated. One method of establishing a correspondence between facial features in the image and the ones on the model may be to detect correspondences for the corners of the lips, corners of the eyes, tip of the nose, and ear lobes. In a morphable model, using the estimation procedure described in the referenced SIGGRAPH 1999 article, the process may also estimate a texture map for the face and the lighting conditions associated with the face at portrait capture. The process attempts to create a rendered image of the face model under the estimated pose and lighting conditions that is as similar to the original portrait image as possible.

Render 2D Image of Face

After 3D pose and shape parameters are estimated and a completed 3D model for the face is made, the makeover program may render a 2D image of the face at different orientations and with different lighting. This process is also described in the referenced SIGGRAPH 1999, cited above. The projection surface patches denoting skin regions of the 3D face model to pixels in the image may be treated as a 2D binary mask and subsequently used in skin detection, as described elsewhere herein.

As may be well known in the graphic arts, the method may be designed to handle some occlusions—such as if the image may be of a face in partial profile to the camera, then part of the face may be occluded and the non-occluded part may be used to estimate the occluded part.

Accessory Modeling

The makeover program may also be configured to provide a library of accessories, such as detailed herein, to accessorize the makeover image. Images of accessories may be captured at different camera angles to allow for application of correctly angled accessories to faces angled to the camera within the portrait. For each camera angle, the accessory may be captured under multiple lighting conditions so as to match the lighting on the accessory to that in the face image. The preferred looks created with rotated accessories may be photo-realistic and lifelike because the makeover program may use the 3D models of the accessories. Accessory models may include shape and texture maps, reflectance maps, and material properties so that given a set of scene rendering conditions such as lights, viewpoint, other objects, and camera parameters, an image of the 3D accessory can then be graphically rendered. The 3D accessory model may be positioned relative to the 3D face model either by a user or automatically by the makeover program software, such that earrings are placed on ear lobes; glasses are placed with the bridge of the nose; and so on.

Rendering function 105 may be configured to rotate the makeover item to match a rotation of the face in the portrait. Rendering function 105 may be also configured to normalize pixel resolutions associated with the portrait and the makeover item. Furthermore, rendering function 105 may be configured to flip a makeover item about an axis to match the light direction of a portrait as detected by the color detection function. Application of accessories such as glasses and jewelry may be added to the look by rendering function 105 and shared with others using one of the following algorithms, or other algorithms with similar affect, which are in keeping with the spirit of the makeover program.

The result may be a rendering of the accessory at an appropriate position, scale and orientation so that it may be placed on the face in the image. The rendering may account for occlusion of part of the accessory by the face. For example, the earpiece of a pair of glasses may be partially occluded by a face at an angle to the camera. Likewise, the effect of lighting on the accessory may be photorealistically rendered because the shadows cast by the face onto the accessory may be captured by this process. The rendering process described here may produce an image of the accessory and an alpha mask. The accessory image may then be composted onto the original face image to produce an image of the face with the accessory.

Rotation of Accessories

The makeover program may also be configured to provide a library of accessories, such as detailed here, to accessorize the makeover image. Images of accessories may be captured at different camera angles to allow for application of correctly angled accessories to faces angled to the camera within the portrait. For each camera angle, the accessory may be captured under multiple lighting conditions so as to match the lighting on accessory to that in the face image. The preferred looks created with rotated accessories may be photorealistic and lifelike because the makeover program may use the 3D models of the accessories. Accessory models may include shape and texture maps, reflectance maps, and material properties so that given a set of scene rendering conditions such as lights, viewpoint, other objects, and camera parameters, an image of the 3D accessory may then be graphically rendered. The 3D accessory model may be positioned relative to the 3D face model either by a user or automatically by the makeover program software, such that earrings are placed on ear lobes; glasses are placed with the bridge of the nose; and so on.

Rendering Various Makeover Items

The following provides detailed description of specific methods for image rendering of various makeover items in one or more embodiments of the invention. Various embodiments may also offer Makeover Editors and render other types of makeover items, and methods for such rendering in various embodiments may follow one or more of the methods described in this section.

Lip Gloss Rendering

The lip gloss feature may be illustrated as three layers—a) Gloss Layer b) Color Layer and c) Sheer Layer. The Gloss Layer may be created as a monochromatic layer where it derives its color from the color of light falling on the lips. It may be assumed that the grayscale brightness (i.e., V in HSV color space) of a pixel in the lip region may be directly related to the cosine of the angle made by the surface normal at that pixel with the light source direction. The gloss value at each pixel may be computed using Equation 2, where, $V(x,y)$ is the grayscale value of pixel $(x,y)$ and $Max(V)$ is the maximum grayscale value of all pixels in $V(x,y)$. "Amount" controls the amount of gloss, while lobe_size controls the width of the specular lobe. Amount may be defaulted by the makeover program, and/or selected by the user or recommended by the makeover program in one or more embodiments of the makeover program, as described elsewhere herein.

$$g(x,y)=\text{Amount}*[V(x,y)/\text{Max}(V)]^\wedge(1/\text{lobe\_size}) \qquad \text{Equation 2:}$$

The Color Layer $c(x,y)$ may be created by transforming the color pixels in the lip region. The hue of each pixel may be set to the hue of the desired lip gloss color, which may be selected by the user or recommended by the makeover program, as described elsewhere herein, in one or more embodiments of the makeover program. The saturation and brightness of the pixels may be scaled based on the average saturation and maximum brightness of pixels and the saturation and brightness of the desired lip gloss color. See Equation 3, where h, s, and v are the hue, saturation and value of the lip gloss color; H, S, and V are the hue, saturation, and value components of the lip region; and Hout, Sout, Vout are the hue, saturation and value components of color layer c. Equation 4 shows the computation of sScale and vScale used in Equation 3, where: avgS=average saturation of all pixels in the lip region; maxV=maximum value of all pixels in the lip region; and sAmount and vAmount are set to 0.25

$$H\text{out}(x,y)=h;$$

$$S\text{out}(x,y)=s\text{Scale}*S(x,y)$$

$$V\text{out}(x,y)=v\text{Scale}*V(x,y) \qquad \text{Equation 3:}$$

$$s\text{Scale}=(s*s\text{Amount}/\text{avg}S)+1-s\text{Amount};$$

$$v\text{Scale}=(v*v\text{Amount}/\text{max}V)+1-v\text{Amount}; \qquad \text{Equation 4:}$$

The Gloss Layer may also be calculated by adding the Gloss Layer and Color Layers with consideration to the color of the light source, as $g(x,y)L+c(x,y)$ where L is the color of the light source. The Sheer Layer may be implemented as a transparency using an alpha-blending of the Gloss Layer with subsequent layers.

Under-Eye Concealer

Concealer is a makeup product typically applied under the eyes to hide dark circles and bagginess. Concealer in a virtual makeover may be simulated by color and transparency effects added to the image. A target region under each eye may be identified for applying under-eye concealer by taking into account the information gained during the preprocessing step of identifying the location of each eye in the portrait. A source region of skin area having the same shape, size, and approximately the same shading as the target region may be identified directly below the target region in the image. The source and target regions may then be merged, resulting in the appearance of removing the dark circles and or bags under the eyes using Equation 5, where r, g, b=red, green and blue channels of color; $U(x,y)$=pixel at location $(x,y)$ of the final under-eye concealer layer; alpha=transparency of the concealer's color; $s(x,y)$=pixel at location $(x,y)$ of the source region; $t(x,y)$=pixel at location $(x,y)$ of the target region; and c=color of the concealer defaulted by the makeover program, selected by the user or recommended by the makeover program in one or more embodiments of the makeover program, as described elsewhere herein.

$$U(x,y,r)=\text{alpha}*\text{Max}(s(x,y,r),t(x,y,r))+(1-\text{alpha})*c(r)$$

$$U(x,y,g)=\text{alpha}*\text{Max}(s(x,y,g),t(x,y,g))+(1-\text{alpha})*c(g)$$

$$U(x,y,b)=\text{alpha}*\text{Max}(s(x,y,b),t(x,y,b))+(1-\text{alpha})*c(b) \qquad \text{Equation 5:}$$

Foundation

After the skin region is detected using methods described elsewhere herein, the image pixels within the skin region may be smoothed using a filter whose support size may be proportional to the size of the face in pixels. The smoothed skin may be denoted by $S(x,y)$. Foundation color may be added to the smoothed skin using Equation 6, where r, g, b=red, green and blue channels of color; $F(x,y)$=pixel at location $(x,y)$ of the final foundation layer; alpha=coverage of the color; $S(x,y)$=pixel at location $(x,y)$ of the smoothed skin image; and c=color of the foundation product defaulted by the makeover program, selected by the user or recommended by the makeover program in one or more embodiments of the makeover program, as described elsewhere herein.

$$F(x,y,r)=\text{alpha}*S(x,y,r)+(1-\text{alpha})*c(r) \qquad \text{Equation 6:}$$

The foundation layer may be blended with the face layer using an alpha mask that may be represented by a 1 at skin regions, a 0 at non-skin regions, and may be gradually diminished from 1 to 0 over several pixels at the boundary of skin and non-skin regions.

Contact Lenses

The application of colored contact lens may be rendered using a method comprising first determining a region for application of the colored contact lens by segmenting the areas of pupil, iris, and "whites" of the eye within the eye regions that may have been identified during the preprocessing step of locating each eye in the portrait. In other embodiments the preprocessing step may have identified the pupil, iris and or whites of the eyes separately, either automatically, semi-automatically, or with user provided input, in various embodiments of the invention. Further, the user may be asked to select a target contact lens color using methods described elsewhere herein, as well as in the related co-pending applications elsewhere herein incorporated by reference. The makeover program may also recommend a target color, or a default color may be applied.

Next, given the target color of the colored contact lenses and the segregation of the iris and pupil areas of the eyes as mentioned above, the makeover program may set the hue and saturation of all pixels in the iris region of each eye to the hue and saturation of the target color. The brightness value of the iris (now contacts) region may provide the texture. In the case of dark eyes, a constant value may be added to the brightness channel in one or more embodiments to produce a desirable result. Finally, the brightness of the contacts region may be scaled such that the average brightness of the region matches the brightness of the target color.

System Architecture Overview

Figure 7:
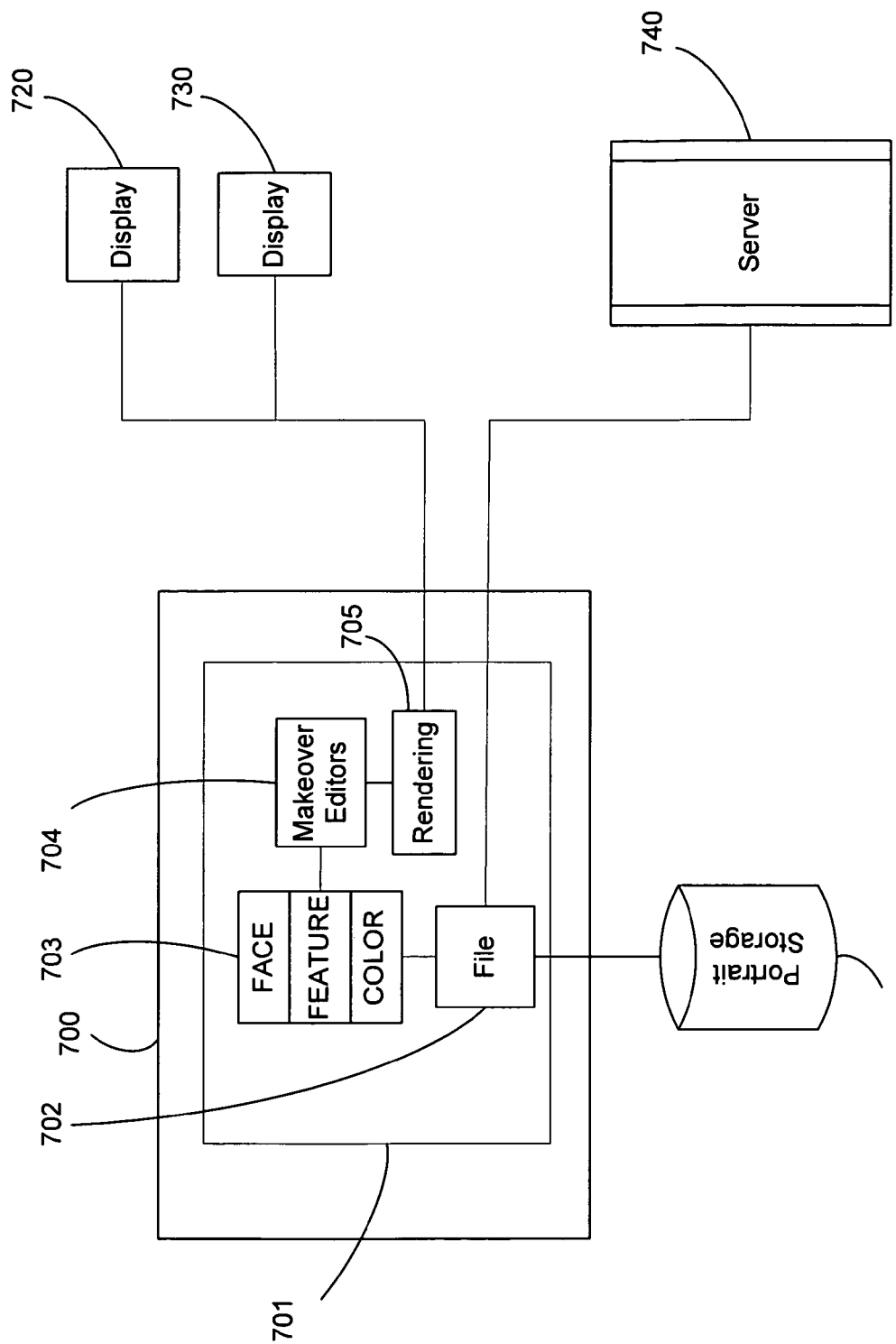
FIG. 7 illustrates exemplary system architecture for one or more embodiments of the invention.

FIG. 7 illustrates an architectural view of one or more embodiments of the system of the invention. The various embodiments may comprise any form of computing device capable of supporting the methods as described herein. One or more embodiments will execute on any computing device capable of accepting user input from any input method known to work with computing devices, such as a keyboard, mouse, touch pad or touch screen, voice data processor, selection buttons, USB connection, game controllers, accelerometer based input detectors, or any other form of computer or computing device input method known by those of skill in the art. Various embodiments of the invention will also comprise computing devices that may vary greatly in capability and size, but will all be capable of displaying data to a user in some visual and graphical form. For example, computing devices supporting the invention may include a desktop, laptop, PDA, handheld computer, kiosk, cellular telephone, projection system, or any computing device supporting a web browser. Computing devices of these types may include displays such as for example computer monitors, LCD, CRT, plasma, television displays of all types, touch screens, projection displays, heads up displays, see through displays, wearable displays and the like.

Various embodiments of the system further comprise software-based instructions that perform detection functions such as detectors 702, 703, 705 and one or more makeover editors 704 that execute on one or more computing devices such as computer 700. Computer 700 supports the embodiments of the system of the invention by having a computer-usable (or computer-readable) memory medium comprising computer-readable program code 701 embodied there. The computer-readable program code includes file function 702 that interfaces with portrait storage element 710. Portrait storage element 710 may be configured to store at least one portrait in volatile or non-volatile memory. While shown coupled to computer 700 in the exemplary embodiments of FIG. 7, portrait storage element 710 may be located and/or physically coupled to computer 700, server 740, when present, or another computing device capable of communicating stored data to computer 700. The computer-readable program code of one or more embodiments of the invention may also comprises detection function 703 that comprises one or more detection functions, such as a face detection function, a face-feature detection function and color detection function as illustrated as aspects of detection function 703 in FIG. 7 and described elsewhere herein. In addition, the computer-readable program code may also include one or more makeover editor functions 401-404 and rendering function 705. Display 720 may be used to present graphical user interface elements, photorealistic computer rendered portraits and makeover items as by computer 700 to a first user. Display 730 may be used to present the same items rendered by computer 700 to one or more additional users that may join the first user to perform the makeover together, simultaneously, sequentially, or in other ways known to those in the computer communication arts.

One or more embodiments of the invention may comprise server 740, while other embodiments may be self-contained, depending on the capabilities of computer 700 and the desired embodiment of the invention. When present, server 740 may store makeovers from one or more users; said makeovers may be shared with other users of the invention. Server 740 may provide the computer-readable program code to computer 700, or the code may be installed on or resident on computer 700. In one or more embodiments, computer 700 and server 740 act in a client-server model to perform the methods of the various embodiments of the invention. Computer 700 and computer server 740 are connected by any informational communications means known to those of skill in the art, for example but not limited to: wired connections such at Ethernet, USB, fiberoptic or other wired connections; wirelessly connected, such as for example but not limited to various well-known wireless protocols such as the IEEE 802 family of protocols, wireless telephony; or other similar such informational coupling mechanisms as will be known to those of skill in the art.

File function 702 may be configured in one or more embodiments with various methods of obtaining a portrait such as for example: uploading an image file over an Internet or similar connection, selection of a portrait from a library of portraits available on the host computer, cut and paste of an image into a user interface associated with the makeover program, receipt of an image through a gifting mechanism that may be part of the makeover program, through email received by a user of the makeover program into a local email account, directly from a digital camera that is connected to a computer, photos acquired using a web camera, photo acquired using a mobile phone camera and electronically sent to the server or any other methods well-known by those of ordinary skill in the art. The portrait may be stored local to computer 700 in storage element 710 for example, or may be stored remotely on server 740.

Rendering function 705 may be configured to use the skin tone and the light color and direction to combine the makeover item to the face in the image at photorealistic offsets associated with the facial boundaries and the eye and mouth boundaries to generate a look for a user. In one or more embodiments of the invention, rendering function 705 may be configured to smooth the skin tone associated with the face in the portrait, for example using Gaussian smoothing. Rendering function 705 may be configured to blend the skin tone associated with the face with the makeover item using at least one non-zero alpha transparency value in one or more embodiments to allow for photorealistic blending of areas that avoid a cutout looking rendering. Rendering function 705 may be configured to apply the makeover item, for example concealer, to a first area beneath eye boundaries through utilization of skin tone from a second area that resides at an offset from the first area. For example, for individuals with dark areas beneath their eyes, a slightly lower portion of skin beneath the dark area may be used to lighten the dark area beneath the eyes. Rendering function 105 may be configured to blend the skin tone with the makeover item for example hair having an associated hairstyle and hair color at a boundary between the face and the hair. This allows for photorealistic rendering that avoids a cutout looking rendering. Rendering function 705 may be configured to alter a shape associated with the makeover item for example hair where the shape may be modified via control points displayed in the at least one makeover editor function 704. This may allow a hair image to be shaped around the face, ears, or other facial features in a photorealistic manner that customizes a hairstyle image for use in a particular portrait while minimizing graphic artifacts in the hair's appearance.

Computer System Architecture

The method described here is not limited as to the type of computer it may run upon and may for instance operate on any generalized computer system that has the computational ability to execute the methods described herein and can display the results of the users choices on a display means. The computer typically includes at least a keyboard, a display device such as a monitor, and a pointing device such as a mouse. The computer also typically comprises a random access memory, a read only memory, a central processing unit and a storage device such as a hard disk drive. In some embodiments of the interface, the computer may also comprise a network connection that allows the computer to send and receive data through a computer network such as the Internet. Mobile computer platforms such as cell phones, Personal Desktop Assistants (PDAs), kiosks, games boxes or any other computational device may also qualify as a computer system capable of executing the methods described herein.

In various embodiments, the present invention may be implemented as a method, apparatus, or article of manufacture using standard "programming and/or engineering techniques to produce software, firmware, hardware, or any combination thereof. The term "article of manufacture" (or alternatively, "computer program product") as used herein is intended to encompass a computer program accessible from any computer-readable device, carrier, memory or other media. In addition, the software in which various embodiments are implemented may be accessible through the transmission medium, for example, from a server over the network. The article of manufacture in which the code is implemented also encompasses transmission media, such as the network transmission line and wireless transmission media. Thus, the article of manufacture also comprises the medium in which the code is embedded. Those skilled in the art will recognize that many modifications may be made to this configuration without departing from the scope of the present invention.

Embodiments of the system use makeover editors embodied in software that may execute on one or more computers having a computer usable memory medium and computer readable program code. The computer readable program code may include an input function, a face detection function, a face-feature detection function, a color detection function, at least one makeover editor and a rendering function. The input function may be configured in one or more embodiments to obtain a portrait. The face detection function may be configured in one or more embodiments to detect facial boundaries of a face in the portrait. The face-feature detection function may be configured to detect eye and mouth boundaries within the facial boundaries. The color detection function may be configured to detect skin tone and light color and direction associated with the face in the portrait. The various makeover editor functions are configured to provide makeover items to apply with respect to the face. The rendering function may be configured to use the skin tone and the light color and direction to combine the makeover item to the face photorealistically at offsets associated with the facial boundaries and the eye and mouth boundaries to generate a look for a user.

The makeover editors enable virtual makeover editing on a local computer system. Alternatively, for high-speed network connection based users, embodiments of the system may use server based look editing. In one or more embodiments, the user uploads the look and the portrait to a server for sharing the resulting makeover with other users. Other embodiments of the invention also allow multiple users to modify the same look for a particular portrait at the same time.

One or more embodiments of the invention may be implemented in the form of one or more computer programs that when executed in computer memory may cause one or more computer processors to initiate the methods and processes described herein. The files assembled to makeup the software program may be stored on one or more computer-readable medium and retrieved when needed to carry out the programmed methods and processes described herein. Within the scope of a computer-implemented embodiment of the invention, readers should note that one or more embodiments of the invention may comprise computer programs, data and other information further comprising but not limited to: sets of computer instructions, code sequences, configuration information, data and other information in any form, format or language usable by a general purpose computer or other data processing device, such that when such a computer or device contains, is programmed with, or has access to said computer programs, the data and other information transforms said general purpose computer into a machine capable of performing the methods and processes described herein, and specifically such as those described above.

Various embodiments of the invention may be implemented as a method, apparatus, or article of manufacture using standard programming and/or engineering techniques to produce software, firmware, hardware, computer-readable media or any combination thereof. The term "article of manufacture" (or alternatively, "computer program product,") as used herein is intended to encompass a computer program of any form accessible from any computer-readable device, carrier or media. In addition, the software in which various embodiments are implemented may be accessible through a transmission medium, such as for example, from a server over the network. The article of manufacture in which the makeover program is implemented may also employ transmission media, such as a network transmission line and/or a wireless transmission media. Those skilled in the art will recognize that many modifications may be made to this configuration without departing from the scope of the invention.

A computer-readable medium suitable to provide computer readable instructions and/or computer readable data for the methods and processes described herein may be any type of magnetic, optical, electrical or other storage medium including disk, tape, CD, DVD, flash drive, thumb drive, storage card, distributed storage or any other memory device, location, approach or other storage medium or technique known to those of skill in the art.

In one or more embodiments of the invention, the methods described here may not be limited as to the type of computer it may run upon and may for instance operate on any generalized computer system that has the computational ability to execute the methods described herein and can display the results of the user's choices on one or more display devices. Display devices appropriate for providing interaction with the invention described herein includes, but is not limited to, computer monitors, cell phones, PDAs, televisions, or any other form of computer controllable output display. As used herein, a computer system refers to but is not limited to any type of computing device, including its associated computer software, data, peripheral devices, communications equipment and any required or desired computers that may achieve direct or indirect communication with a primary computing device.

In one or more embodiments of the invention, a general-purpose computer may be utilized to implement one or more aspects of the invention. In one or more embodiments of the invention, the computer may include various input and output means, including but not limited to a keyboard or other textual input devices, a display device such as a monitor or other display screen, and a pointing device and/or user selection indicator such as a mouse, keypad, touch screen, pointing device, or other known input/output devices known to those of skill in the art. The general-purpose computer described herein may include one or more banks of random access memory, read only memory, and one or more central processing unit(s). The general-purpose computer described herein may also include one or more data storage device(s) such as a hard disk drive, or other computer readable medium discussed above. An operating system that executes within the computer memory may provide an interface between the hardware and software. The operating system may be responsible for managing, coordinating and sharing of the limited resources within the computer. Software programs that run on the computer may be performed by an operating system to provide the makeover program of the invention with access to the resources needed to execute. In other embodiments the makeover program may run stand-alone on the processor to perform the methods described herein.

In one or more embodiments of the invention, the method(s) described herein, when loaded on or executing through or by one or more general purpose computer(s) described above, may transform the general-purpose computer(s) into a specially programmed computer able to perform the method or methods described herein. In one or more embodiments of the invention, the computer-readable storage medium(s) encoded with computer program instructions that, when accessed by a computer, may cause the computer to load the makeover program instructions to a memory there accessible, thereby creates a specially programmed computer able to perform the methods described herein as a specially programmed computer.

The specially programmed computer of the invention may also comprise a connection that allows the computer to send and/or receive data through a computer network such as the Internet or other communication network. Mobile computer platforms such as cellular telephones, Personal Desktop Assistants (PDAs), other hand-held computing devices, digital recorders, wearable computing devices, kiosks, set top boxes, games boxes or any other computational device, portable, personal, real or virtual or otherwise, may also qualify as a computer system or part of a computer system capable of executing the methods described herein as a specially programmed computer.

Figure 8:
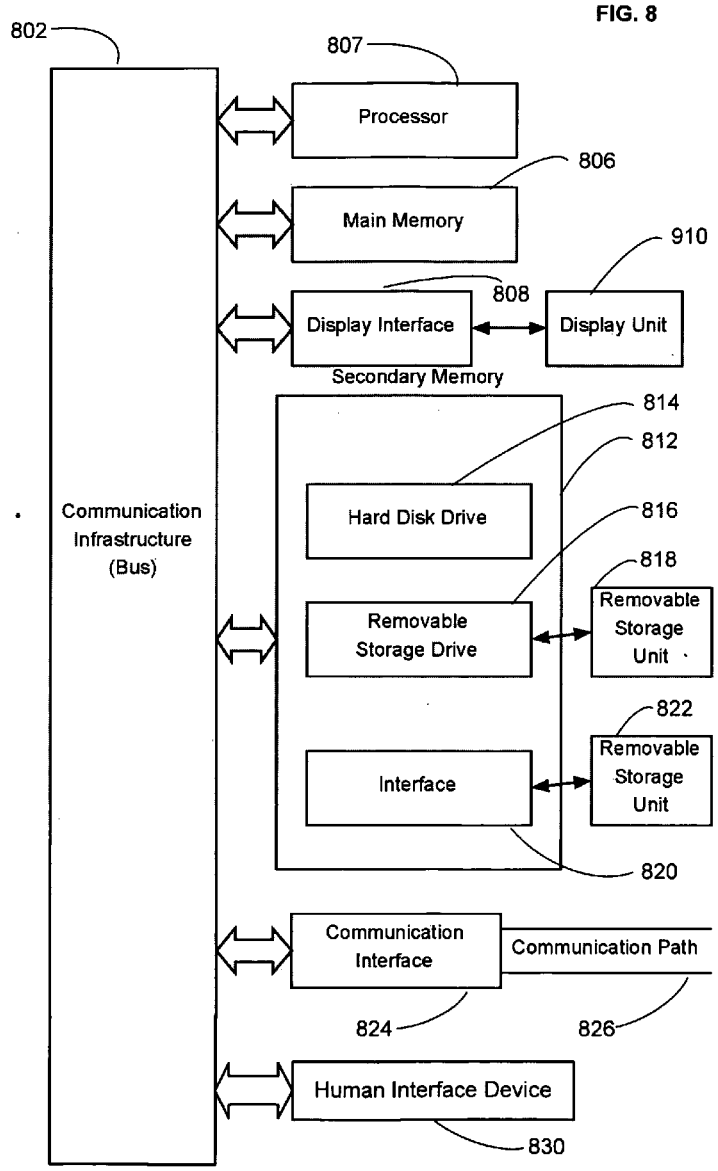
FIG. 8 illustrates a computer system that, when programmed with the various methods described, may implement the invention.

FIG. 8 depicts a general-purpose computer and peripherals, when programmed as described herein, may operate as a specially programmed computer capable of implementing one or more methods, apparatus and/or systems of the invention. Processor 807 may be coupled to bi-directional communication infrastructure 802 such as Communication Infrastructure System Bus 802. Communication Infrastructure 802 may generally be a system bus that provides an interface to the other components in the general-purpose computer system such as Processor 807, Main Memory 806, Display Interface 808, Secondary Memory 812 and/or Communication Interface 824.

Main memory 806 may provide a computer readable medium for accessing and executed stored data and applications. Display Interface 808 may communicate with Display Unit 810 that may be utilized to display outputs to the user of the specially-programmed computer system. Display Unit 810 may comprise one or more monitors that may visually depict aspects of the computer program to the user. Main Memory 806 and Display Interface 808 may be coupled to Communication Infrastructure 802, which may serve as the interface point to Secondary Memory 812 and Communication Interface 824. Secondary Memory 812 may provide additional memory resources beyond main Memory 806, and may generally function as a storage location for computer programs to be executed by Processor 807. Either fixed or removable computer-readable media may serve as Secondary Memory 812. Secondary Memory 812 may comprise, for example, Hard Disk 814 and Removable Storage Drive 816 that may have an associated Removable Storage Unit 818. There may be multiple sources of Secondary Memory 812 and systems of the invention may be configured as needed to support the data storage requirements of the user and the methods described herein. Secondary Memory 812 may also comprise Interface 820 that serves as an interface point to additional storage such as Removable Storage Unit 822. Numerous types of data storage devices may serve as repositories for data utilized by the specially programmed computer system of the invention. For example, magnetic, optical or magnetic-optical storage systems, or any other available mass storage technology that provides a repository for digital information may be used.

Communication Interface 824 may be coupled to Communication Infrastructure 802 and may serve as a conduit for data destined for or received from Communication Path 826. A Network Interface Card (NIC) is an example of the type of device that once coupled to Communication Infrastructure 802 may provide a mechanism for transporting data to Communication Path 826. Computer networks such Local Area Networks (LAN), Wide Area Networks (WAN), Wireless networks, optical networks, distributed networks, the Internet or any combination thereof are some examples of the type of communication paths that may be utilized by the specially program computer system of the invention. Communication Path 826 may comprise any type of telecommunication network or interconnection fabric that can transport data to and from Communication Interface 824.

To facilitate user interaction with the specially programmed computer system of the invention, one or more Human Interface Devices (HID) 830 may be provided. Some examples of HIDs that enable users to input commands or data to the specially programmed computer of the invention may comprise a keyboard, mouse, touch screen devices, microphones or other audio interface devices, motion sensors or the like, as well as any other device able to accept any kind of human input and in turn communicate that input to Processor 807 to trigger one or more responses from the specially programmed computer of the invention are within the scope of the system of the invention.

While FIG. 8 depicts a physical device, the scope of the system of the invention may also encompass a virtual device, virtual machine or simulator embodied in one or more computer programs executing on a computer or computer system and acting or providing a computer system environment compatible with the methods and processes of the invention. Where a virtual machine, process, device or otherwise performs substantially similarly to that of a physical computer system of the invention, such a virtual platform will also fall within the scope of a system of the invention, notwithstanding the description herein of a physical system such as that in FIG. 8.

One or more embodiments of the invention are configured to enable the specially programmed computer of the invention to take the input data given and transform it into a virtual makeover by applying one or more of the methods and/or processes of the invention as described herein. Thus the methods described herein are able to transform the raw input data, such as a digital portrait, to a makeover image, using the system of the invention to result in an output of the system as a revised portrait, using the specially programmed computer as described herein. Particularly, the system of the invention may be programmed to acquire a digital image, display the digital image to a user, accept user selections or other input regarding desired alterations to the digital image, alter the digital image, and display the revised digital image to the user.

Performance Considerations

Some graphic web-based applications are single-threaded. For example, Adobe Flash may be used to render images for display in using a single-threaded implementation. However, processor intensive interactive graphic applications such as the makeover program described herein may not perform well in a single-threaded implementation. For example, when a user changes a hairstyle by dragging a hair control point to manipulate the shape of the hairstyle, a processor intensive task of "warping" the hairstyle image may consume significant processor time, producing unsatisfactory response time and possibly freezing mouse movement on the screen. The following describes at least two techniques, "backgrounding" and multi-resolution rendering, that may be used to improve the interactivity (responsiveness) of the application to graphically intense image rendering as may be required in the makeover program described herein.

Backgrounding

In one or more embodiments of the invention may make use of a technique referred to as "backgrounding." Backgrounding may be described by way of an example as follows. Suppose we have a block of code that executes in one second. While the block of code is executing, the processor will not register a mouse movement or a mouse click, and the application will appear frozen to the user. If this block of code is partitioned into smaller pieces so that the biggest piece executes in 100 ms, the processor can be freed up to handle other processes such as displaying mouse movements or performing other interactive tasks in slices between the code blocks, sometimes several times before the entire code block executes. In one or embodiments of the invention, this may be achieved by dividing large code block into smaller functions and storing the functions in an array, for example. The functions may then be executed in order, freeing the processor for interrupts at fixed period of time between two successive function calls.

Multi-Resolution Rendering

In one or more embodiments of the invention, a multi-resolution rendering process may be utilized to render an image faster at lower resolution. At one-half resolution, there may be as few as one-quarter the number of the pixels to render than in the original image, and thus the image may be displayed as much as four times faster. At one quarter resolution, there may be only $\frac{1}{16}^{th}$ the number of pixels to render, and so the image may render sixteen times faster. During interactive operations to the image such as warping hairstyle shape or adjusting the position of an eye shadow layer, timely rendering of the image may provide more satisfactory response and give the user better feedback regarding the reshaping or replacement process, which may be more important than seeing the result at high resolution.

Thus, for example, in the task of reshaping a hairstyle by moving control points, as described elsewhere herein, as a control point is dragged many mouse-drag events may be sent to the application in quick succession. Thus, hairstyle warping may generally be a processor consuming process. The rendering method processing mouse-drag events may be overwhelmed at the highest resolution due to the computationally intensive nature of the operation. Instead, the hairstyle layer may be warped, as described elsewhere herein, and the result displayed at a lower resolution than the rest of the image. For example, in one or more embodiments a one-quarter resolution may produce satisfactory results. At one-quarter resolution, for example, a single rendering of a hairstyle warp may be completed before the next mouse event is received by the process, and the full resolution of the image layer may only be rendered if necessary or upon completion of the mouse-drag event queue. For example, if a hair control point is dragged from position A to position B to position C, the rendering method will be invoked on the first event, when the control point is moved from position A to position B. The first rendering may be done at quarter resolution. The makeover program may then check to see if a render at full resolution is warranted, for example using a look-ahead function on the mouse drag event queue. If no additional events are to be processed after reaching position B, the hairstyle may then be rendered at the next higher resolution. If, however, the control point has next moved from position B to position C, a higher resolution rendering for position B is unnecessary and may be skipped.

Combining Techniques to Improve Rendering Performance

Backgrounding and multi-resolution rendering may be used individually or together improve responsiveness and preserve user interactivity. Better performance gains may be achieved when these techniques are utilized in combination, as follows.

The image layers may be understood to have an order and a dependency. For the purposes as used herein, the term "order" may be understood to mean that image layers have a predefined order in which they are drawn when being displayed. For example in one or more embodiments of the invention, hairstyle may be though of as the top-most layer and foundation (makeup) may be thought of as the bottom-most layer. Further, dependency may be understood to mean that a given image layer may be "dependent" on one or more other image layers for its rendering. For example, a blush layer may be dependent on a foundation layer meaning that each time the foundation layer changes the blush layer will need to be redrawn, because the appearance of blush is dependent on the foundation that lies beneath blush. However, the eye shadow and lipstick layers may not be dependent on the foundation layer, because the eye shadow layer and lipstick layer do not intersect.

Figure 9:
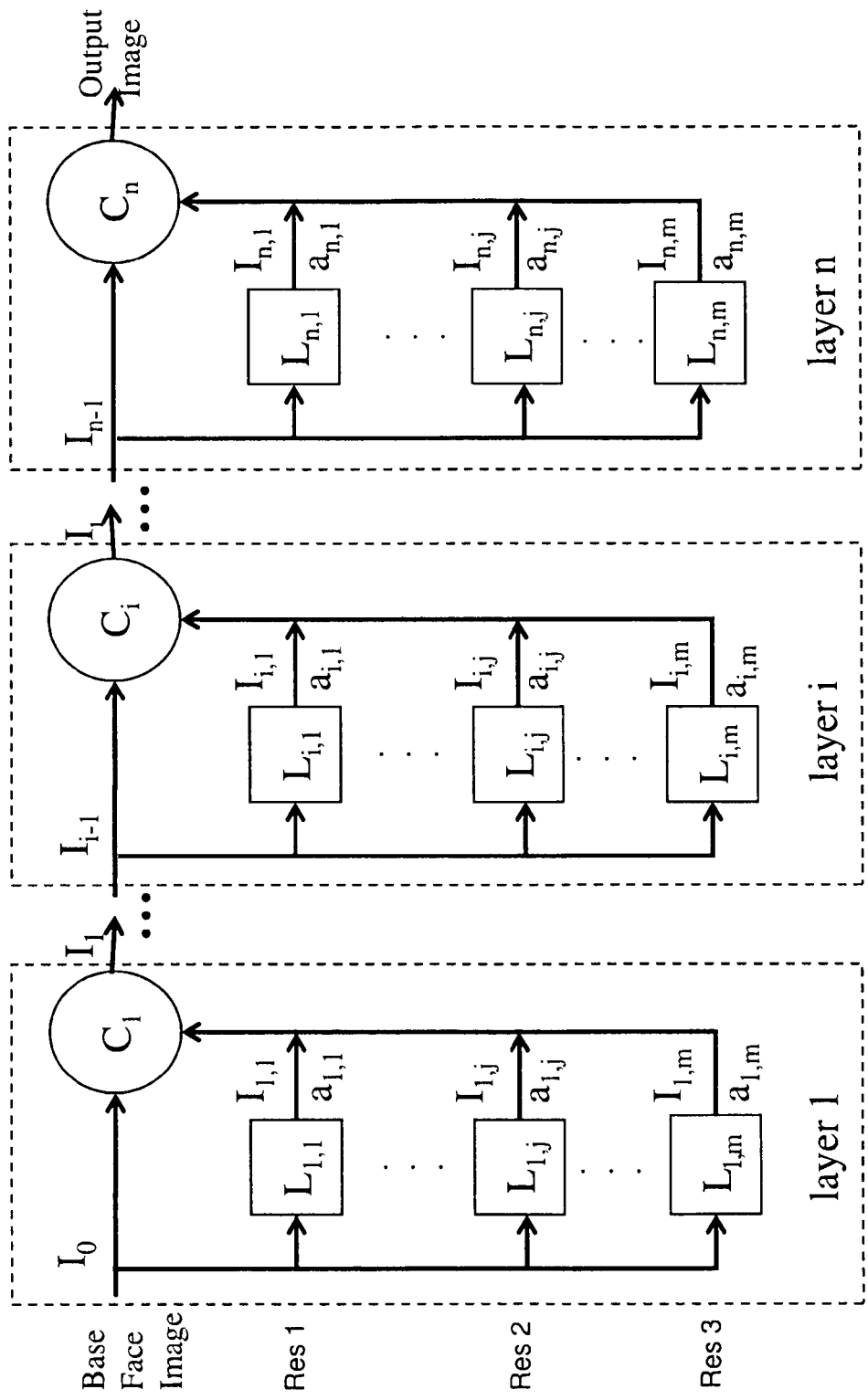
FIG. 9 illustrates a multi-resolution rendering process in accordance with one or more embodiments of the invention, showing that rendering may proceed from lowest to highest resolution, and for each resolution from the bottom layer to the top layer.

Rendering may proceed from lowest to highest resolution, and for each resolution from the bottom layer to the top layer. Referring to FIG. 9 as an example in one or more embodiments of the invention, rendering may start with Base Face Image (I). Layer 1 may be the lowest layer (for example, a Foundation Layer.) Layer i may be a blush layer, and Layer n may be hair layer. The output of rendering Layer i is image $I_i$. The rendering of each Layer i may comprise multiple passes, as illustrated in FIG. 9.

The processing illustrated in FIG. 9 may be traced in the following exemplary description. One or more embodiments of the invention may process layers as follows and as illustrated in FIG. 9. Block $L_{i,j}$ renders layer i at resolution j. Resolution 1 (Res 1) is the lowest resolution and Resolution m is the highest or full resolution. Resolution 1 might be quarter resolution, Resolution j (Res 2) might be half resolution, and Resolution m (Res 3) might be full resolution. Block $L_{i,j}$ takes in the output image $I_{i-1}$ of the previous layer and the particular makeup element and renders that element. For example, it might render lipstick just over the lip region as described elsewhere in this patent. The output of $L_{i,j}$ is an image $I_{i,j}$ and Combining Information $a_{i,j}$ (e.g., an alpha mask) that is used by $C_i$. Block $C_i$ is a combiner, and it combines $L_A$ and the image output of Rendering Block $L_{i,j}$ using the combing information from $L_{i,j}$. One way of combining the layers is alpha-blending which is given by the equation $I_i = a_{i,j} I_{i-1} + (1-a_{i,j}) I_{i,j}$, but other ways of combining layers can be used.

Rendering may then proceed as described in the following pseudo-code example:

FOR j=1 to m
  FOR i=1 to n
  Use block Li,j to produce $I_{i,j}$ and $a_{i,j}$ from $I_{i-1}$;
  Use block $C_i$ to produce the output of layer i at resolution j by combining $I_{i-1}$ with $I_{i,j}$ using $a_{i,j}$;
  Check for a UI event;
  IF there is a UI event resulting in a change to the information used to render layer k where k<I
  THEN
    Abort rendering;
    Restart loop with j=1 and i=k;
  END
END The rendering of one or a set of successive layers may constitute a step of the rendering with backgrounding process.

After rendering layer i at resolution j, the backgrounding process may check for a UI event. If a UI event causes a change to the makeup information (for example, position and/or color of some makeup makeover item) for a given layer k that is lower than layer i (that is, where k<i), then rendering may be aborted and restarted at the lowest resolution at layer k.

The makeover program of one or more embodiments of the invention may support rendering at one-quarter scale, one-half scale, and full scale, however an arbitrary number of rendering resolutions may be used.

Performance of rendering layers with dependencies, as described above, may be improved by looping through the layers and determining if the current layer is independent of any layer which has changed since the previous rendering of the current layer. If so, then the current layer does not have to be rendered.

While the invention disclosed has been described by means of specific embodiments and applications thereof, numerous modifications and variations may be made thereto by those skilled in the art without departing from the scope of the invention as described and set forth in the claims attached hereto.

What is claimed is:

1. A non-transitory computer-readable medium comprising computer program product for creating and sharing a personalized virtual makeover image, said computer program product comprising computer readable instructions, wherein execution of said computer readable instructions by one or more processors causes said one or more processors to:
preprocess an image using a computing device;
accept a first input selecting a makeover item from a set of makeover items associated with a predefined order;
obtain locations of placement points for said makeover item on said image;
automatically transform said makeover item using affine transformation so that its position conforms to said locations of said placement points;
create a first graphics layer and a first mask for said transformed makeover item;
accept a second input selecting at least one additional makeover item from said set of makeover items, obtain locations of placement points for said at least one additional makeover item on said image, automatically transform said at least one additional makeover item using affine transformation so that its position conforms to said locations of said placement points for said at least one additional makeover item, and create at least one additional graphics layer and a corresponding mask for said transformed at least one additional makeover item;
merge said first graphics layer and said at least one additional graphics layer onto said image in a layering order using said predefined order to create a virtual makeover image on a display comprising adjustment handles on said makeover item and said at least one additional makeover item for adjustment and transformation control of said makeover item and said at least one additional makeover item, wherein said first graphics layer and said at least one additional graphics layer are operated upon individually to adjust and transform said makeover item and said at least one additional makeover item using said adjustment handles;
accept further inputs from said adjustment handles to generate an adjusted and transformed first graphics layer and an at least one adjusted and transformed additional graphics layer; and
generate the virtual makeover image by rendering said adjusted and transformed first graphics layer through said first mask and said at least one adjusted and transformed additional graphics layer through said corresponding mask onto said image in said layering order using said predefined order.

2. The non-transitory computer-readable medium of claim 1, wherein said set of makeover items comprises at least one face layer makeover item, at least one mouth layer makeover item and at least one eye layer makeover item, wherein said predefined order indicates layering of said at least one face layer makeover item below said at least one mouth layer makeover item and said least one eye layer makeover item.

3. The non-transitory computer-readable medium of claim 2, wherein said set of makeover items further comprises at least one hair layer makeover item, wherein said predefined order indicates layering of said at least one hair layer makeover item above said at least one face layer makeover item, said at least one mouth layer makeover item and said least one eye layer makeover item.

4. The non-transitory computer-readable medium of claim 1, wherein said placement points are automatically detected.

5. The non-transitory computer-readable medium of claim 1, wherein said set of makeover items comprises at least one foundation and at least one blush, wherein said predefined order indicates layering of said at least one foundation below said at least one blush.

6. The non-transitory computer-readable medium of claim 1, wherein said create a first layer for said transformed makeover item comprises applying said transformed makeover item through a skin mask.

7. The non-transitory computer-readable medium of claim 1, wherein said virtual makeover image is displayed on a display coupled to said computing device.

8. A non-transitory computer-readable medium comprising computer program product for creating a personalized virtual makeover image, said computer program product comprising computer readable instructions, wherein execution of said computer readable instructions by one or more processors causes said one or more processors to:
   preprocess a base image using a computing device;
   accept a first input selecting a hairstyle for application to said base image;
   obtain locations of placement points for said hairstyle on said base image;
   automatically transform said hairstyle using affine transformation so that its position conforms to said locations of said placement points, wherein said transform results in warping said hairstyle;
   generate a hair layer and a mask for said transformed hairstyle;
   accept a second input selecting at least one additional makeover item from a set of makeover items associated with a predefined order, obtain locations of placement points for said at least one additional makeover item on said base image, automatically transform said at least one additional makeover item using affine transformation so that its position conforms to said locations of said placement points for said at least one additional makeover item, and generate at least one additional graphics layer and a corresponding mask for said transformed at least one additional makeover item;
   merge said hair layer and said at least one additional graphics layer on said base image in a layering order using said predefined order to create a virtual makeover image on a display comprising adjustment handles on said hairstyle and said at least one additional makeover item for adjustment and transformation control of said hairstyle and said at least one additional makeover item, wherein said hair layer and said at least one additional graphics layer are operated upon individually to adjust and transform said hairstyle and said at least one additional makeover item using said adjustment handles;
   accept further inputs from said adjustment handles to generate an adjusted and transformed hair layer and an at least one adjusted and transformed additional graphics layer; and
   render said adjusted and transformed hair layer through said mask and said at least one adjusted and transformed additional graphics layer through said corresponding mask onto said base image in said layering order using said predefined order to create the virtual makeover image.

9. The non-transitory computer-readable medium of claim 8, wherein said transformation control comprises a global transformation control.

10. The non-transitory computer-readable medium of claim 9, wherein said global transformation comprises six degrees of freedom.

11. The non-transitory computer-readable medium of claim 10, wherein said global transformation comprises an affine transformation.

12. The non-transitory computer-readable medium of claim 9, wherein said global transformation control comprises a bounding box.

13. The non-transitory computer-readable medium of claim 8, wherein said transformation control comprises a local transformation control.

14. The non-transitory computer-readable medium of claim 13, wherein said local transformation control comprises a control for morphing said hairstyle.

15. The non-transitory computer-readable medium of claim 13, wherein said local transformation control comprises a control for orienting said hairstyle.

16. An article of manufacture comprising:
   a computing device;
   said computing device informationally coupled to at least one display device;
   said computing device informationally coupled to at least one input device;
   said computing device informationally coupled to at least one tangible form of computer data storage;
   said computing device comprising computer-readable program instructions, said computer readable program instructions comprising a virtual makeover method, said virtual makeover method comprising:
      preprocessing an image on a computing device;
      accepting a first input selecting a makeover item from a set of makeover items associated with a predefined order;
      obtaining locations of placement points for said makeover item on said image;
      automatically transforming said makeover item using affine transformation so that its position conforms to said locations of said placement points;
      generating a graphics layer and a first mask for said transformed makeover item;
      accepting a second input selecting at least one additional makeover item from said set of makeover items, obtaining locations of placement points for said at least one additional makeover item on said image, automatically transforming said at least one additional makeover item using affine transformation so that its position conforms to said locations of said placement points for said at least one additional makeover item, and generating at least one additional graphics layer and a corresponding mask for said at least one additional makeover item;
      merging said graphics layer and said at least one additional graphics layer onto said image in a layering order using said predefined order to create a virtual makeover image on a display comprising adjustment handles on said makeover item and said at least one additional makeover item for adjustment and transformation control of said makeover item and said at least one additional makeover item, wherein said first graphics layer and said at least one additional graphics layer are operated upon individually to adjust and transform said makeover item and said at least one additional makeover item using said adjustment handles;

accepting further inputs from said adjustment handles to generate an adjusted and transformed graphics layer and at least one adjusted and transformed additional graphics layer; and rendering said adjusted and transformed graphics layer through said first mask and said at least one adjusted and transformed additional graphics layer through said corresponding mask onto said image in said layering order using said predefined order to create the virtual makeover image.

17. The article of manufacture of claim 16 wherein said computing device further comprises a kiosk.

18. The article of manufacture of claim 16 wherein said computing device further comprises a handheld computing device.

19. The article of manufacture of claim 16 wherein said computing device further comprises a toy.

20. A virtual makeover computer system comprising:

a computing device informationally coupled to a user input device and a display device;

a portrait stored in a tangible computer readable memory medium coupled to said computing device;

said computing device comprising a computer usable memory medium specially programmed with computer readable program code, wherein said computer readable program code comprises a method to:

detect a face in said portrait, said face delineated by a facial boundary;

detect facial features boundaries within said facial boundary;

detect color properties associated with said face in said portrait; obtain a plurality of makeover items from a recommended list of makeover items to apply with respect to said face, wherein said plurality of makeover items are associated with a predefined order, wherein said recommended list is based on said color properties, said facial features, user preferences, user attributes, or combinations thereof;

at least one image processing function configured to automatically transform each one of said plurality of makeover items using affine transformation so that its position conforms to locations of at least one of said facial boundary and said facial features and further configured to generate a plurality of graphics layers and a plurality of masks, wherein each one of said plurality of graphics layers and a corresponding one of said plurality of masks represent one of said plurality of makeover items, wherein said image processing function is further configured to merge said plurality of graphics layers onto said portrait in a layering order using said predefined order to create a virtual makeover image on a display comprising adjustment handles on said plurality of makeover items for adjustment and transformation control of said plurality of makeover items, wherein said plurality of graphics layers is operated upon individually to adjust and transform each one of said plurality of makeover items using said adjustment handles, wherein said image processing function is further configured to accept further inputs from said adjustment handles and generate an adjusted and transformed plurality of graphics layers; and a rendering function configured to create the virtual makeover image from said adjusted and transformed plurality of graphics layers through said plurality of masks onto said portrait, wherein said adjusted and transformed plurality of graphics layers is rendered in said layering order using said predefined order.

21. The virtual makeover computer system of claim 20 wherein said face detection is performed automatically.

22. The virtual makeover computer system of claim 20 wherein said facial features detection is performed automatically.

23. The virtual makeover computer system of claim 20 wherein said facial features detection is performed semi-automatically.

24. The virtual makeover computer system of claim 20 wherein said facial features boundaries comprise boundaries of a mouth within said face in said portrait.

25. The virtual makeover computer system of claim 20 wherein said facial features boundaries comprise boundaries of eyes within said face in said portrait.

26. The virtual makeover computer system of claim 20 wherein said color properties comprise skin tone.

27. The virtual makeover computer system of claim 20 wherein said color properties comprise light color.

28. The virtual makeover computer system of claim 20 wherein said color properties comprise light direction.

29. The virtual makeover computer system of claim 20 wherein a color space that decomposes color into chromacity and luminance is used to detect said color properties.

30. The virtual makeover computer system of claim 20 wherein said computing device is coupled to a computer server over a computer network.

31. The virtual makeover computer system of claim 20 wherein said computing device is coupled to a computer server over a World Wide Web via an Internet; and wherein said makeover image is displayed in a web browser.

32. The virtual makeover computer system of claim 20 wherein said plurality of graphics layers is operated upon by at least two users.

33. The virtual makeover computer system of claim 20 wherein said plurality of graphics layers is operated upon simultaneously by at least two users.

34. The virtual makeover computer system of claim 20 wherein said rendering function is further configured to:

obtain a stored look describing at least one makeover item;

automatically transform said stored look to said detected facial features of said detected facial boundary; and apply said stored look to said portrait before rendering said makeover image.

35. A virtual makeover computer system comprising:

a computer server;

a computing device informationally coupled to said computer server, said computing device coupled to a user input device and a display device;

a portrait stored in a tangible computer readable memory medium coupled to said computing device;

said computing device comprising a computer usable memory medium specially programmed with computer readable program code, wherein said computer readable program code comprises:

a face detection function configured to automatically detect facial boundaries of a face in said portrait;

a facial feature detection function configured to detect facial features boundaries within said facial boundaries;

a recommendation engine configured to provide a plurality of makeover items to apply with respect to said face, wherein said plurality of makeover items are associated with a predefined order;

at least one image processing function configured to automatically transform each one of said plurality of makeover items using affine transformation so that its position conforms to locations of at least one of said facial boundaries and said facial features and further configured to generate a plurality of graphics layers and a plurality of masks, wherein each one of said plurality of graphics layers and a corresponding one of said plurality of masks represent one of said plurality of makeover items, wherein said image processing function is further configured to merge said plurality of graphics layers onto said portrait in a layering order using said predefined order to create a virtual makeover image on a display comprising adjustment handles on said plurality of makeover items for adjustment and transformation control of said plurality of makeover items, wherein said plurality of graphics layers is operated upon individually to adjust and transform each one of said plurality of makeover items using said adjustment handles, wherein said image processing function is further configured to accept further inputs from said adjustment handles and generate an adjusted and transformed plurality of graphics layers; and a rendering function configured to create the virtual makeover image comprising said adjusted and transformed plurality of graphics layers through said plurality of masks onto said portrait, wherein said adjusted and transformed plurality of graphics layers is rendered in said layering order using said predefined order.

36. A virtual makeover computer system comprising:

a computing device informationally coupled to a user input device and a display device;

a portrait stored in a tangible computer readable memory medium coupled to said computing device;

said computing device comprising a computer usable memory medium specially programmed with computer readable program code, wherein said computer readable program code comprises:

a facial boundary detection function for detecting a face in said portrait;

a facial features detection function for detecting facial features within said facial boundary;

a plurality of makeover items to apply with respect to said portrait, wherein said plurality of makeover items are associated with a predefined order;

a recommendation engine configured to generate selected ones from said plurality of makeover items;

at least one image processing function configured to automatically transform each one of said plurality of makeover items using affine transformation so that its position conforms to locations of at least one of said facial boundaries and said facial features and further configured to generate a plurality of graphics layers and a plurality of masks, wherein each one of said plurality of graphics layers and a corresponding one of said plurality of masks represent one of said plurality of makeover items, wherein said image processing function is further configured to merge said plurality of graphics layers onto said portrait in a layering order using said predefined order to create a virtual makeover image on a display comprising adjustment handles on said plurality of makeover items for adjustment and transformation control of said plurality of makeover items, wherein said plurality of graphics layers is operated upon individually to adjust and transform each one of said plurality of makeover items using said adjustment handles, wherein said image processing function is further configured to accept further inputs from said adjustment handles and generate an adjusted and transformed plurality of graphics layers; and a rendering function configured to generate the makeover image by merging said selected ones of said adjusted and transformed plurality of graphics layers through said plurality of masks onto said portrait, wherein said adjusted and transformed plurality of graphics layers is rendered in said layering order using said predefined order.

37. The virtual makeover computer system of claim 36 wherein said selected ones comprise a product.

38. The virtual makeover computer system of claim 36 wherein said selected ones comprise a style.

39. The virtual makeover computer system of claim 36 wherein said selected ones comprise a technique.

40. The virtual makeover computer system of claim 36 wherein said selected ones comprise a color.

41. The virtual makeover computer system of claim 36 wherein said recommendation engine is an expert system.

42. The virtual makeover computer system of claim 36 wherein said recommendation engine is a learning system.

43. The virtual makeover computer system of claim 36 wherein said selected ones are generated by considering said facial features.

44. The virtual makeover computer system of claim 36 wherein said selected ones are generated by considering the personal characteristics of said portrait.

45. The virtual makeover computer system of claim 36 wherein said selected ones are generated by considering popularity of said selected ones.

46. The virtual makeover computer system of claim 36 wherein said selected ones are generated based on a scored gallery of choices.

47. The virtual makeover computer system of claim 36 wherein said selected ones comprise a recommended look.

* * * * *